US010669530B2

(12) United States Patent
Soucaille et al.

(10) Patent No.: US 10,669,530 B2
(45) Date of Patent: Jun. 2, 2020

(54) CLOSTRIDIUM ACETOBUTYLICUM STRAINS UNABLE TO PRODUCE HYDROGEN AND USEFUL FOR THE CONTINUOUS PRODUCTION OF CHEMICALS AND FUELS

(71) Applicants: INSTITUT NATIONAL DES SCIENCES APPLIQUEES, Toulouse (FR); INSTITUT NATIONAL DE LA RECHERCHE AGRONOMIQUE, Paris (FR); CENTRE NATIONAL DE LA RECHERCHE SCIENTIFIQUE (CNRS), Paris (FR)

(72) Inventors: Philippe Soucaille, Deyme (FR); Ngoc-Phuong-Thao Nguyen, Toulouse (FR); Benjamin Percheron, Toulouse (FR); Christian Croux, Auzeville Tolosane (FR); Isabelle Meynial-Salles, Fourquevaux (FR)

(73) Assignees: CENTRE NATIONAL DE LA RECHERCHE SCIENTIFIQUE, Paris (FR); INSTITUT NATIONAL DES SCIENCES APPLIQUEES, Toulouise (FR); INSTITUT NATIONAL DE A RECHERCHE AGRONOMIQUE, Paris (FR)

( * ) Notice: Subject to any disclaimer, the term of this patent is extended or adjusted under 35 U.S.C. 154(b) by 289 days.

(21) Appl. No.: 15/508,746

(22) PCT Filed: Sep. 18, 2015

(86) PCT No.: PCT/EP2015/071518
§ 371 (c)(1),
(2) Date: Mar. 3, 2017

(87) PCT Pub. No.: WO2016/042160
PCT Pub. Date: Mar. 24, 2016

(65) Prior Publication Data
US 2017/0240869 A1 Aug. 24, 2017

(30) Foreign Application Priority Data

Sep. 18, 2014 (EP) .................................... 14306442

(51) Int. Cl.
| C12P 7/16 | (2006.01) |
| C12P 7/04 | (2006.01) |
| C12N 9/10 | (2006.01) |
| C12N 9/02 | (2006.01) |
| C12P 7/06 | (2006.01) |
| C12P 7/54 | (2006.01) |
| C12P 7/24 | (2006.01) |
| C12P 7/18 | (2006.01) |

(52) U.S. Cl.
CPC ......... *C12N 9/1029* (2013.01); *C12N 9/0067* (2013.01); *C12P 7/04* (2013.01); *C12P 7/065* (2013.01); *C12P 7/16* (2013.01); *C12P 7/18* (2013.01); *C12P 7/24* (2013.01); *C12P 7/54* (2013.01); *C12Y 112/01004* (2013.01); *C12Y 203/01016* (2013.01); *Y02E 50/10* (2013.01); *Y02E 50/17* (2013.01)

(58) Field of Classification Search
None
See application file for complete search history.

(56) References Cited

FOREIGN PATENT DOCUMENTS

EP 2267141 A1 12/2010

OTHER PUBLICATIONS

Cooksley et al., "Targeted mutagenesis of the Clostridium acetobutylicum acetone-butanol-ethanol fermentation pathway," Metabolic Engineering, 14:630-641 (2012).
Dusseaux et al., "Metabolic engineering of Clostridium acetobutylicum ATCC 824 for the high-yield production of a biofuel composed of an isopropanol/butanol/ethanol mixture," Metabolic Engineering, 18:1-8 (2013).
Extended European Search Report for EP 14306442.6 dated Mar. 6, 2015 (6 pages).
Gonzalez-Pajuelo et al., "Metabolic engineering of Clostridium acetobutylicum for the industrial production of 1,3-propanediol from glycerol," Metabolic Engineering, 7:329-336 (2005).
Harris et al., "Northern, Morphological, and Fermentation Analysis of spo0A Inactivation and Overexpression in Clostridium acetobutylicum ATCC 824," Journal of Bacteriology, 184(13):3586-3597 (2002).
Heap et al., "The ClosTron: Mutagenesis in Clostridium refined and streamlined," Journal of Microbiological Methods, 80:49-55 (2010).
Kim et al., "Control of Carbon and Electron Flow in Clostridium acetobutylicum Fermentations: Utilization of Carbon Monoxide to Inhibit Hydrogen Production and to Enhance Butanol Yields," Applied and Environmental Microbiology, 48 (4):764-770 (1984).
McAnulty et al., "Genome-scale modeling using flux ratio constraints to enable metabolic engineering of clostridial metabolism in silico," BMC Systems Biology, 6:42 (15 pages) (2012).
Mann et al., "Thiolase Engineering for Enhanced Butanol Production in Clostridium acetobutylicum," Biotechnology and Bioengineering, 110(3):887-897 (2013).
Nolling et al., "Genome Sequence and Comparative Analysis of the Solvent-Producing Bacterium Clostridium acetobutylicum," Journal of Bacteriology, 183(16):4823-4838 (2001).
Raynaud et al., "Molecular characterization of the 1,3-propanediol (1,3-PD) operon of Clostridium butyricum," PNAS, 100(9):5010-5015 (2003).

(Continued)

*Primary Examiner* — Channing S Mahatan
(74) *Attorney, Agent, or Firm* — Arrigo, Lee, Guttman & Mouta-Bellum LLP

(57) ABSTRACT

The present invention relates to a new strain of *Clostridium acetobutylicum* modified to be unable to produce hydrogen and its use for the continuous production of bulk chemicals such as lactate, 1,3-propanediol, ethanol, butanol, isobutanol, 1,3-butanediol, acetate, acetone, isopropanol, 3-hydroxy-3-methylbutyrate and isobutene at high yield.

23 Claims, 8 Drawing Sheets
Specification includes a Sequence Listing.

(56) References Cited

OTHER PUBLICATIONS

Sonderegger et al., "Evolutionary Engineering of *Saccharomyces cerevisiae* for Anaerobic Growth on Xylose," Applied and Environmental Microbiology, 69(4):1990-1998 (2003).
Soni et al., "Continuous acetone-butanol fermentation: influence of vitamins on the metabolic activity of Clostridium acetobutylicum," Appl. Microbiol. Biotechnol., 27:1-5 (1987).
Lutke-Eversloh, Tina, "Application of new metabolic engineering tools for Clostridium acetobutylicum," Appl. Microbiol. Biotechnol., 98:5823-5837 (2014).
Weber et al., "Trends and challenges in the microbial production of lignocellulosic bioalcohol fuels," Appl. Microbiol. Biotechnol., 87:1303-1315 (2010).
Jang et al., "Metabolic engineering of Clostridium acetobutylicum for butyric acid production with high butyric acid selectivity," Metabolic Engineering, 23:165-174 (2014).

SEQUENCE LISTING

```
<160> NUMBER OF SEQ ID NOS: 109

<210> SEQ ID NO 1
<211> LENGTH: 43
<212> TYPE: DNA
<213> ORGANISM: Artificial Sequence
<220> FEATURE:
<223> OTHER INFORMATION: pcat-Upp-F primer

<400> SEQUENCE: 1
aaaaaaggat ccctttttcg gcaagtgttc aagaagttat taa          43

<210> SEQ ID NO 2
<211> LENGTH: 37
<212> TYPE: DNA
<213> ORGANISM: Artificial Sequence
<220> FEATURE:
<223> OTHER INFORMATION: pcat-Upp-R primer

<400> SEQUENCE: 2
aaaaaaggat ccgtgagcaa aaggccagca aaaggcc                 37

<210> SEQ ID NO 3
<211> LENGTH: 43
<212> TYPE: DNA
<213> ORGANISM: Artificial Sequence
<220> FEATURE:
<223> OTHER INFORMATION: p15A-F primer

<400> SEQUENCE: 3
aaaaggatcc ttaataagat gatcttcttg agatcgtttt ggt          43

<210> SEQ ID NO 4
<211> LENGTH: 36
<212> TYPE: DNA
<213> ORGANISM: Artificial Sequence
<220> FEATURE:
<223> OTHER INFORMATION: p15A-R primer

<400> SEQUENCE: 4
aaaagtcgac gcgctagcgg agtgtatact ggctta                  36

<210> SEQ ID NO 5
<211> LENGTH: 46
<212> TYPE: DNA
<213> ORGANISM: Artificial Sequence
<220> FEATURE:
<223> OTHER INFORMATION: eryUpp-F primer
```

<400> SEQUENCE: 5
aaaagtcgac tctacgacca aaagtataaa acctttaaga actttc        46

<210> SEQ ID NO 6
<211> LENGTH: 53
<212> TYPE: DNA
<213> ORGANISM: Artificial Sequence
<220> FEATURE:
<223> OTHER INFORMATION: eryUpp-R primer

<400> SEQUENCE: 6
tattttacat tctttatttt ttattttgta ccgaataatc tatctccagc atc        53

<210> SEQ ID NO 7
<211> LENGTH: 62
<212> TYPE: DNA
<213> ORGANISM: Artificial Sequence
<220> FEATURE:
<223> OTHER INFORMATION: upp-Teradhe2-F primer

<400> SEQUENCE: 7
gattattcgg tacaaaataa aaataaaga atgtaaaata gtctttgctt cattatatta        60
gc        62

<210> SEQ ID NO 8
<211> LENGTH: 51
<212> TYPE: DNA
<213> ORGANISM: Artificial Sequence
<220> FEATURE:
<223> OTHER INFORMATION: teradhe2-R primer

<400> SEQUENCE: 8
aaaaggatcc aagataaaaa acaagagtaa aatgtaaaat agtctatgtg c        51

<210> SEQ ID NO 9
<211> LENGTH: 38
<212> TYPE: DNA
<213> ORGANISM: Artificial Sequence
<220> FEATURE:
<223> OTHER INFORMATION: upp-1 primer

<400> SEQUENCE: 9
aaaagccggc tcctgatcta ttaattcttg atgaaccc        38

<210> SEQ ID NO 10
<211> LENGTH: 57
<212> TYPE: DNA
<213> ORGANISM: Artificial Sequence
<220> FEATURE:
<223> OTHER INFORMATION: upp-2 primer

<400> SEQUENCE: 10
ggggaggcct aaaaggggg attgcataaa taaaagggc tgaaaaataa atttcag        57

<210> SEQ ID NO 11
<211> LENGTH: 56
<212> TYPE: DNA
<213> ORGANISM: Artificial Sequence
<220> FEATURE:
<223> OTHER INFORMATION: upp-3 primer

<400> SEQUENCE: 11
cccccttttt aggcctcccc ttatttcatt cctccattgt atttttttc tatttg        56

```
<210> SEQ ID NO 12
<211> LENGTH: 42
<212> TYPE: DNA
<213> ORGANISM: Artificial Sequence
<220> FEATURE:
<223> OTHER INFORMATION: upp-4 primer

<400> SEQUENCE: 12
aaaagttaac gctattatga ataggttaaa taagtcagct gg                    42

<210> SEQ ID NO 13
<211> LENGTH: 30
<212> TYPE: DNA
<213> ORGANISM: Artificial Sequence
<220> FEATURE:
<223> OTHER INFORMATION: upp-0 primer

<400> SEQUENCE: 13
aatacaagca aagagaatag gctatgtgcc                                  30

<210> SEQ ID NO 14
<211> LENGTH: 30
<212> TYPE: DNA
<213> ORGANISM: Artificial Sequence
<220> FEATURE:
<223> OTHER INFORMATION: upp-5 primer

<400> SEQUENCE: 14
aatacaagca aagagaatag gctatgtgcc                                  30

<210> SEQ ID NO 15
<211> LENGTH: 29
<212> TYPE: DNA
<213> ORGANISM: Artificial Sequence
<220> FEATURE:
<223> OTHER INFORMATION: upp-F primer

<400> SEQUENCE: 15
ggcatatgaa gtaacaagag aaatgcagc                                   29

<210> SEQ ID NO 16
<211> LENGTH: 28
<212> TYPE: DNA
<213> ORGANISM: Artificial Sequence
<220> FEATURE:
<223> OTHER INFORMATION: upp-R primer

<400> SEQUENCE: 16
ataatctatc tccagcatct ccaagacc                                    28

<210> SEQ ID NO 17
<211> LENGTH: 42
<212> TYPE: DNA
<213> ORGANISM: Artificial Sequence
<220> FEATURE:
<223> OTHER INFORMATION: cac-1 primer

<400> SEQUENCE: 17
aaaggatcca tgcacactca taaatttact gtaggaagtc tg                    42

<210> SEQ ID NO 18
<211> LENGTH: 51
<212> TYPE: DNA
<213> ORGANISM: Artificial Sequence
<220> FEATURE:
<223> OTHER INFORMATION: cac-2 primer
```

<400> SEQUENCE: 18
ggggaggcct aaaaaggggg gtcccaaata atatttgcca tagtaaccac c        51

<210> SEQ ID NO 19
<211> LENGTH: 50
<212> TYPE: DNA
<213> ORGANISM: Artificial Sequence
<220> FEATURE:
<223> OTHER INFORMATION: cac-3 primer

<400> SEQUENCE: 19
cccccttttt aggcctcccc tcgaacttat tagaatgatt aagattccgg          50

<210> SEQ ID NO 20
<211> LENGTH: 39
<212> TYPE: DNA
<213> ORGANISM: Artificial Sequence
<220> FEATURE:
<223> OTHER INFORMATION: cac-4 primer

<400> SEQUENCE: 20
aaaggatcct cattaaattt cctccatttt aagcctgtc                      39

<210> SEQ ID NO 21
<211> LENGTH: 35
<212> TYPE: DNA
<213> ORGANISM: Artificial Sequence
<220> FEATURE:
<223> OTHER INFORMATION: cac-0 primer

<400> SEQUENCE: 21
gtgatataat tttcctttaa atggaggagg atctg                          35

<210> SEQ ID NO 22
<211> LENGTH: 30
<212> TYPE: DNA
<213> ORGANISM: Artificial Sequence
<220> FEATURE:
<223> OTHER INFORMATION: cac-5 primer

<400> SEQUENCE: 22
gccgttaata gacattataa ttccattggc                                30

<210> SEQ ID NO 23
<211> LENGTH: 32
<212> TYPE: DNA
<213> ORGANISM: Artificial Sequence
<220> FEATURE:
<223> OTHER INFORMATION: cac-F primer

<400> SEQUENCE: 23
gaattcttaa aaatatttgg atcattaagc gg                             32

<210> SEQ ID NO 24
<211> LENGTH: 32
<212> TYPE: DNA
<213> ORGANISM: Artificial Sequence
<220> FEATURE:
<223> OTHER INFORMATION: cac-R primer

<400> SEQUENCE: 24
gttgtattgg aatctttgtt attatttctc cc                             32

<210> SEQ ID NO 25
<211> LENGTH: 50

<212> TYPE: DNA
<213> ORGANISM: Artificial Sequence
<220> FEATURE:
<223> OTHER INFORMATION: thl-1 primer

<400> SEQUENCE: 25
aaaaggatcc aagcagttaa tgaaaagaat atttttatta caggaaatac          50

<210> SEQ ID NO 26
<211> LENGTH: 57
<212> TYPE: DNA
<213> ORGANISM: Artificial Sequence
<220> FEATURE:
<223> OTHER INFORMATION: thl-2 primer

<400> SEQUENCE: 26 gttatttttta acaatacttt aggccttacg gggtaacaga taaaccattt caatcta   57

<210> SEQ ID NO 27
<211> LENGTH: 66
<212> TYPE: DNA
<213> ORGANISM: Artificial Sequence
<220> FEATURE:
<223> OTHER INFORMATION: thl-3 primer

<400> SEQUENCE: 27
aatttaggag gttagttaga aggcctaaag tattgttaaa ataactctg tagaattata   60 aattag                                                            66

<210> SEQ ID NO 28
<211> LENGTH: 44
<212> TYPE: DNA
<213> ORGANISM: Artificial Sequence
<220> FEATURE:
<223> OTHER INFORMATION: thl-4 primer

<400> SEQUENCE: 28
aaaaggatcc aagttaacaa tcatttctat tacgctttgt ttcc                  44

<210> SEQ ID NO 29
<211> LENGTH: 29
<212> TYPE: DNA
<213> ORGANISM: Artificial Sequence
<220> FEATURE:
<223> OTHER INFORMATION: thl-0 primer

<400> SEQUENCE: 29
acatggagat acgactacaa catttgctg                                   29

<210> SEQ ID NO 30
<211> LENGTH: 34
<212> TYPE: DNA
<213> ORGANISM: Artificial Sequence
<220> FEATURE:
<223> OTHER INFORMATION: thl-5 primer

<400> SEQUENCE: 30 ttcttttat tgcagttgca tttattaaaa atgc                              34

<210> SEQ ID NO 31
<211> LENGTH: 30
<212> TYPE: DNA
<213> ORGANISM: Artificial Sequence
<220> FEATURE:
<223> OTHER INFORMATION: thl-F primer

<400> SEQUENCE: 31
tggaacattt caagagaaga acaagatgag                                30

<210> SEQ ID NO 32
<211> LENGTH: 32
<212> TYPE: DNA
<213> ORGANISM: Artificial Sequence
<220> FEATURE:
<223> OTHER INFORMATION: thl-R primer

<400> SEQUENCE: 32
gctcctccat ttacatttac tttattcata tc                             32

<210> SEQ ID NO 33
<211> LENGTH: 42
<212> TYPE: DNA
<213> ORGANISM: Artificial Sequence
<220> FEATURE:
<223> OTHER INFORMATION: Hyd-1 primer

<400> SEQUENCE: 33
aaaggatccg tttttcttaa tatttaccat attgcacctc cc                  42

<210> SEQ ID NO 34
<211> LENGTH: 48
<212> TYPE: DNA
<213> ORGANISM: Artificial Sequence
<220> FEATURE:
<223> OTHER INFORMATION: Hyd-2 primer

<400> SEQUENCE: 34
atatctctta agctgttagt ttccattata gtcatatctg caccaaag            48

<210> SEQ ID NO 35
<211> LENGTH: 50
<212> TYPE: DNA
<213> ORGANISM: Artificial Sequence
<220> FEATURE:
<223> OTHER INFORMATION: Hyd-3 primer

<400> SEQUENCE: 35
cagatatgac tataatggaa actaacagct aagagatat tgatgcatcc           50

<210> SEQ ID NO 36
<211> LENGTH: 37
<212> TYPE: DNA
<213> ORGANISM: Artificial Sequence
<220> FEATURE:
<223> OTHER INFORMATION: Hyd-4 primer

<400> SEQUENCE: 36
aaaggatccc tggtacatca gtatacgaaa caatgcc                        37

<210> SEQ ID NO 37
<211> LENGTH: 33
<212> TYPE: DNA
<213> ORGANISM: Artificial Sequence
<220> FEATURE:
<223> OTHER INFORMATION: Hyd-0 primer

<400> SEQUENCE: 37
catgttctat tgttactatg gaagaggtag tag                            33

<210> SEQ ID NO 38
<211> LENGTH: 29

<210> SEQ ID NO 38
<211> LENGTH: 29
<212> TYPE: DNA
<213> ORGANISM: Artificial Sequence
<220> FEATURE:
<223> OTHER INFORMATION: Hyd-5 primer

<400> SEQUENCE: 38
gcagttatta taaatgctgc tactagagc                                    29

<210> SEQ ID NO 39
<211> LENGTH: 25
<212> TYPE: DNA
<213> ORGANISM: Artificial Sequence
<220> FEATURE:
<223> OTHER INFORMATION: Hyd-F primer

<400> SEQUENCE: 39
gaagctactg aacttttagg cagag                                        25

<210> SEQ ID NO 40
<211> LENGTH: 29
<212> TYPE: DNA
<213> ORGANISM: Artificial Sequence
<220> FEATURE:
<223> OTHER INFORMATION: Hyd-R primer

<400> SEQUENCE: 40
ctgcttcata tttttatca ttacaaggc                                     29

<210> SEQ ID NO 41
<211> LENGTH: 39
<212> TYPE: DNA
<213> ORGANISM: Artificial Sequence
<220> FEATURE:
<223> OTHER INFORMATION: ldh-1 primer

<400> SEQUENCE: 41
aaaaggatcc gctttaaaat ttggaaagag gaagttgtg                         39

<210> SEQ ID NO 42
<211> LENGTH: 56
<212> TYPE: DNA
<213> ORGANISM: Artificial Sequence
<220> FEATURE:
<223> OTHER INFORMATION: ldh-2 primer

<400> SEQUENCE: 42
ggggaggcct aaaaggggg ttagaaatct ttaaaaattt ctctatagag cccatc       56

<210> SEQ ID NO 43
<211> LENGTH: 57
<212> TYPE: DNA
<213> ORGANISM: Artificial Sequence
<220> FEATURE:
<223> OTHER INFORMATION: ldh-3 primer

<400> SEQUENCE: 43 ccccttttt aggcctcccc ggtaaaagac ctaaactcca agggtggagg ctaggtc      57

<210> SEQ ID NO 44
<211> LENGTH: 48
<212> TYPE: DNA
<213> ORGANISM: Artificial Sequence
<220> FEATURE:
<223> OTHER INFORMATION: ldh-4 primer

<400> SEQUENCE: 44
aaaaggatcc cccattgtgg agaatattcc aaagaagaaa ataattgc    48

<210> SEQ ID NO 45
<211> LENGTH: 31
<212> TYPE: DNA
<213> ORGANISM: Artificial Sequence
<220> FEATURE:
<223> OTHER INFORMATION: ldh-0 primer

<400> SEQUENCE: 45
cagaaggcaa gaatgtatta agcggaaatg c    31

<210> SEQ ID NO 46
<211> LENGTH: 31
<212> TYPE: DNA
<213> ORGANISM: Artificial Sequence
<220> FEATURE:
<223> OTHER INFORMATION: ldh-5 primer

<400> SEQUENCE: 46
cttcccatta tagctcttat tcacattaag c    31

<210> SEQ ID NO 47
<211> LENGTH: 30
<212> TYPE: DNA
<213> ORGANISM: Artificial Sequence
<220> FEATURE:
<223> OTHER INFORMATION: ldh-F primer

<400> SEQUENCE: 47
ggatttgttg gttcttctac agtatttgcg    30

<210> SEQ ID NO 48
<211> LENGTH: 31
<212> TYPE: DNA
<213> ORGANISM: Artificial Sequence
<220> FEATURE:
<223> OTHER INFORMATION: ldh-R primer

<400> SEQUENCE: 48
cctctataat atccttcact ccgttaattc c    31

<210> SEQ ID NO 49
<211> LENGTH: 30
<212> TYPE: DNA
<213> ORGANISM: Artificial Sequence
<220> FEATURE:
<223> OTHER INFORMATION: ptuk-1 primer

<400> SEQUENCE: 49
ctagaattaa ggatcctaga tgcacgtatg    30

<210> SEQ ID NO 50
<211> LENGTH: 62
<212> TYPE: DNA
<213> ORGANISM: Artificial Sequence
<220> FEATURE:
<223> OTHER INFORMATION: ptuk-2 primer

<400> SEQUENCE: 50
cttctgcaag tgcaagaagt tcgcgacact ggtcgtacac tccctttttac tatttaatta    60
tc    62

<210> SEQ ID NO 51
<211> LENGTH: 52

```
<212> TYPE: DNA
<213> ORGANISM: Artificial Sequence
<220> FEATURE:
<223> OTHER INFORMATION: ptuk-3 primer

<400> SEQUENCE: 51
aagggagtgt acgaccagtg tcgcgaactt cttgcacttg cagaaggtgg ac      52

<210> SEQ ID NO 52
<211> LENGTH: 37
<212> TYPE: DNA
<213> ORGANISM: Artificial Sequence
<220> FEATURE:
<223> OTHER INFORMATION: ptuk-4 primer

<400> SEQUENCE: 52
aaaaggatcc tctaaattct gcaatatatg ccccccc                       37

<210> SEQ ID NO 53
<211> LENGTH: 28
<212> TYPE: DNA
<213> ORGANISM: Artificial Sequence
<220> FEATURE:
<223> OTHER INFORMATION: ptuk-0 primer

<400> SEQUENCE: 53
ataacaggat atatgctctc tgacgcgg                                 28

<210> SEQ ID NO 54
<211> LENGTH: 28
<212> TYPE: DNA
<213> ORGANISM: Artificial Sequence
<220> FEATURE:
<223> OTHER INFORMATION: ptuk-5 primer

<400> SEQUENCE: 54
gatcatcact cattttaaac atggggcc                                 28

<210> SEQ ID NO 55
<211> LENGTH: 28
<212> TYPE: DNA
<213> ORGANISM: Artificial Sequence
<220> FEATURE:
<223> OTHER INFORMATION: ptuk-F primer

<400> SEQUENCE: 55
ctttaaatgc tgtagttgga agaggcgg                                 28

<210> SEQ ID NO 56
<211> LENGTH: 28
<212> TYPE: DNA
<213> ORGANISM: Artificial Sequence
<220> FEATURE:
<223> OTHER INFORMATION: ptuk-R primer

<400> SEQUENCE: 56
taagtaacta acaactccgc ctttgccg                                 28

<210> SEQ ID NO 57
<211> LENGTH: 66
<212> TYPE: DNA
<213> ORGANISM: Artificial Sequence
<220> FEATURE:
<223> OTHER INFORMATION: atob-1 primer

<400> SEQUENCE: 57
```

<210> SEQ ID NO 58
<211> LENGTH: 75
<212> TYPE: DNA
<213> ORGANISM: Artificial Sequence
<220> FEATURE:
<223> OTHER INFORMATION: atob-2 primer

<400> SEQUENCE: 58

```
acttatgaaa tagattgaaa tggtttatct gttaccccgt aggatcctcg aaggtcgacc      60
acccag                                                                  66
```

<210> SEQ ID NO 58
<211> LENGTH: 75
<212> TYPE: DNA
<213> ORGANISM: Artificial Sequence
<220> FEATURE:
<223> OTHER INFORMATION: atob-2 primer

<400> SEQUENCE: 58

```
ctaatttata attctacaga gttattttta acaatacttt ttagtttagt cgttctatta      60
ccatagctat ccctt                                                        75
```

<210> SEQ ID NO 59
<211> LENGTH: 1234
<212> TYPE: DNA
<213> ORGANISM: artificial
<220> FEATURE:
<223> OTHER INFORMATION: Synthetic atoB operon coding for the AtoB
      thiolase of E. coli.

<400> SEQUENCE: 59

```
aggatcctcg aaggtcgacc acccagaata aaggagccat taatgaaaaa ctgcgtgatt    60
gtgagcgctg tgcgtacggc cattggtagc tttaatggta gcctagccag cacaagtgct   120
attgacttag gggctacggt gataaaagct gctatagaac gtgccaaaat tgatagccag   180
cacgtggatg aagtaataat gggtaatgta ttgcaggctg ggttagggca gaacccagct   240
cgtcaagcct tattgaaaag tgggttagcc gaaacggtat gtgggttcac ggtgaacaaa   300
gtgtgcggta gcggtctaaa agcgtagcct ctagctgctc aagctataca agccggtcaa   360
gctcaaagta tagtagctgg gggtatggaa acatgagct tggctccgta cttgctagat   420
gccaaagcca gaagcggtta tcgtctaggg acgggcaag tgtatgacgt gattttaaga   480
gatggattaa tgtgtgctac acatggttat catatgggga taacagctga aaatgtagcc   540
aaagagtacg ggataacacg tgaaatgcaa gatgaattag ctctgcatag ccaacgtaaa   600
gctgccgctg ccatagagag cggtgccttt acggctgaaa ttgtgccagt gaacgtggtg   660
acgcgaaaga aaacattcgt gttcagccag gacgaattcc caaaagctaa cagcacggcc   720
gaagctttgg gtgccctaag accagctttc gataaagccg ggacggtgac agccgggaat   780
gctagcggta taaatgacgg tgccgctgcc ttagtaataa tggaagaaag cgctgcttta   840
gccgccggac taacaccgtt agccagaata aaaagctatg ctagtggtgg agtaccgccg   900
gccctaatgg gtatggggcc ggtgccggct acgcagaaag ctttgcagtt agctgggtta   960
cagttagctg atatagatct aatagaggcc aacgaagcct tgccgcccca attcctagct  1020
gtggggaaaa atttaggatt tgatagcgag aaagtaaacg tgaatggagg ggctattgct  1080
ctagggcatc cgattggtgc tagcggtgcc cgtatattag tgacgctgtt gcatgctatg  1140
caagccagag ataaaacgtt agggttagcc acgttatgta taggaggagg tcaagggata  1200
gctatggtaa tagaacgact aaactaaggc gcca                               1234
```

<210> SEQ ID NO 60
<211> LENGTH: 40
<212> TYPE: DNA
<213> ORGANISM: Artificial Sequence
<220> FEATURE:
<223> OTHER INFORMATION: ilvC-F primer

<400> SEQUENCE: 60
aaaaggatcc tatttttttag gaggaaaagt gttatggaag                    40

<210> SEQ ID NO 61
<211> LENGTH: 50
<212> TYPE: DNA
<213> ORGANISM: Artificial Sequence
<220> FEATURE:
<223> OTHER INFORMATION: ilvC-R primer

<400> SEQUENCE: 61
aaaaggcgcc aaaaaactcg aggcccccta tattatttac tattcgtttg          50

<210> SEQ ID NO 62
<211> LENGTH: 40
<212> TYPE: DNA
<213> ORGANISM: Artificial Sequence
<220> FEATURE:
<223> OTHER INFORMATION: ilvD-F primer

<400> SEQUENCE: 62
aaaactcgag aaggagtgat ttatgtgaat tctgataagg                    40

<210> SEQ ID NO 63
<211> LENGTH: 52
<212> TYPE: DNA
<213> ORGANISM: Artificial Sequence
<220> FEATURE:
<223> OTHER INFORMATION: ilvD-R primer

<400> SEQUENCE: 63
aaaaggcgcc aaaaaaccta ggtcatcact cctttgtact atgaaaaact gc       52

<210> SEQ ID NO 64
<211> LENGTH: 34
<212> TYPE: DNA
<213> ORGANISM: Artificial Sequence
<220> FEATURE:
<223> OTHER INFORMATION: pdc-F primer

<400> SEQUENCE: 64
aaaacctagg tggaggtgac aattttgaag agtg                          34

<210> SEQ ID NO 65
<211> LENGTH: 51
<212> TYPE: DNA
<213> ORGANISM: Artificial Sequence
<220> FEATURE:
<223> OTHER INFORMATION: pdc-R primer

<400> SEQUENCE: 65
aaaaggcgcc tatttaaaat gctatatttt gaactaatta ttttgatttg c        51

<210> SEQ ID NO 66
<211> LENGTH: 57
<212> TYPE: DNA
<213> ORGANISM: Artificial Sequence
<220> FEATURE:
<223> OTHER INFORMATION: ilvCD-pdc-F primer

<400> SEQUENCE: 66
aaagtcgaca agcggccgca aaaaccgcgg tgtggatgga gttaagtcag cagaaag  57

<210> SEQ ID NO 67
<211> LENGTH: 31

```
<212> TYPE: DNA
<213> ORGANISM: Artificial Sequence
<220> FEATURE:
<223> OTHER INFORMATION: ilvCD-pdc-R primer

<400> SEQUENCE: 67
ccatgattac gaattctatg agtcgacatt a                                31

<210> SEQ ID NO 68
<211> LENGTH: 55
<212> TYPE: DNA
<213> ORGANISM: Artificial Sequence
<220> FEATURE:
<223> OTHER INFORMATION: als-F primer

<400> SEQUENCE: 68
aaagcggccg caaaaaacca tggttaaaaa aataatttag agtgagaata agggg       55

<210> SEQ ID NO 69
<211> LENGTH: 41
<212> TYPE: DNA
<213> ORGANISM: Artificial Sequence
<220> FEATURE:
<223> OTHER INFORMATION: als-R primer

<400> SEQUENCE: 69
aaaccgcggc agaattaaaa gctaaataaa atagagtgct g                     41

<210> SEQ ID NO 70
<211> LENGTH: 50
<212> TYPE: DNA
<213> ORGANISM: Artificial Sequence
<220> FEATURE:
<223> OTHER INFORMATION: pthlA-F primer

<400> SEQUENCE: 70
aaagcggccg cttttttaaca aaatatattg ataaaaataa taatagtggg            50

<210> SEQ ID NO 71
<211> LENGTH: 34
<212> TYPE: DNA
<213> ORGANISM: Artificial Sequence
<220> FEATURE:
<223> OTHER INFORMATION: pthlA-R primer

<400> SEQUENCE: 71
aaaccatggt acggggtaac agataaacca tttc                             34

<210> SEQ ID NO 72
<211> LENGTH: 34
<212> TYPE: DNA
<213> ORGANISM: Artificial Sequence
<220> FEATURE:
<223> OTHER INFORMATION: Takt-1 primer

<400> SEQUENCE: 72
aaaggatccc gtaatgttgc agttacagag ggag                             34

<210> SEQ ID NO 73
<211> LENGTH: 65
<212> TYPE: DNA
<213> ORGANISM: Artificial Sequence
<220> FEATURE:
<223> OTHER INFORMATION: Takt-2 primer

<400> SEQUENCE: 73
```

-continued

```
gggggaggcc taaaaagggg gaaaaaaagc tttgttttaa ataagtgttc tttatatact    60
tattc                                                                65

<210> SEQ ID NO 74
<211> LENGTH: 54
<212> TYPE: DNA
<213> ORGANISM: Artificial Sequence
<220> FEATURE:
<223> OTHER INFORMATION: Takt-3 primer

<400> SEQUENCE: 74
cccccttttt aggcctcccc ctataggagg cataagcaat gaaactttt atag           54

<210> SEQ ID NO 75
<211> LENGTH: 36
<212> TYPE: DNA
<213> ORGANISM: Artificial Sequence
<220> FEATURE:
<223> OTHER INFORMATION: Takt-4 primer

<400> SEQUENCE: 75
aaaggatccc ttgcatattc cttgtcctaa aggtcc                              36

<210> SEQ ID NO 76
<211> LENGTH: 66
<212> TYPE: DNA
<213> ORGANISM: Artificial Sequence
<220> FEATURE:
<223> OTHER INFORMATION: Pthl-1 primer

<400> SEQUENCE: 76
acaaagcttt ttttccccct ttttaggttt ttaacaaaat atattgataa aataataat     60 agtggg                                                               66

<210> SEQ ID NO 77
<211> LENGTH: 48
<212> TYPE: DNA
<213> ORGANISM: Artificial Sequence
<220> FEATURE:
<223> OTHER INFORMATION: Pthl-2 primer

<400> SEQUENCE: 77
cttatgcctc ctataggggg aggtacgggg taacagataa accatttc                 48

<210> SEQ ID NO 78
<211> LENGTH: 29
<212> TYPE: DNA
<213> ORGANISM: Artificial Sequence
<220> FEATURE:
<223> OTHER INFORMATION: Takt-0 primer

<400> SEQUENCE: 78
ggattatatg aacttacatc aaagtgctc                                      29

<210> SEQ ID NO 79
<211> LENGTH: 26
<212> TYPE: DNA
<213> ORGANISM: Artificial Sequence
<220> FEATURE:
<223> OTHER INFORMATION: Takt-5 primer

<400> SEQUENCE: 79
catccacttt gataacctgc catccg                                         26
```

```
<210> SEQ ID NO 80
<211> LENGTH: 42
<212> TYPE: DNA
<213> ORGANISM: Artificial Sequence
<220> FEATURE:
<223> OTHER INFORMATION: orfh-F primer

<400> SEQUENCE: 80
aaaaaaaaat cgataatatg gaacccgaat tccggcattc ac          42

<210> SEQ ID NO 81
<211> LENGTH: 43
<212> TYPE: DNA
<213> ORGANISM: Artificial Sequence
<220> FEATURE:
<223> OTHER INFORMATION: orfh-R primer

<400> SEQUENCE: 81
aaaaaaaaaa gcttctttgg acgtagtttg cccatagatg aac         43

<210> SEQ ID NO 82
<211> LENGTH: 48
<212> TYPE: DNA
<213> ORGANISM: Artificial Sequence
<220> FEATURE:
<223> OTHER INFORMATION: xfp-F primer

<400> SEQUENCE: 82
aaaaaaaagg cgccttatac atgccactgc aattagtta tttctggc     48

<210> SEQ ID NO 83
<211> LENGTH: 82
<212> TYPE: DNA
<213> ORGANISM: Artificial Sequence
<220> FEATURE:
<223> OTHER INFORMATION: xfp-R primer

<400> SEQUENCE: 83
aaaaaaaagg atccatgaat tcataattaa tgattataaa tttaggagga atattatgca   60
aagtataata ggaaaacata ag                                            82

<210> SEQ ID NO 84
<211> LENGTH: 117
<212> TYPE: DNA
<213> ORGANISM: Artificial Sequence
<220> FEATURE:
<223> OTHER INFORMATION: pfk-F primer

<400> SEQUENCE: 84
ccctcactaa agggactagt cctgcaggtt taaacgaatt cgcccttagg cctctcgagt   60
taaaagtagg tgttttgtac ataataatat cagaaggtaa acacataatt actatgg      117

<210> SEQ ID NO 85
<211> LENGTH: 76
<212> TYPE: DNA
<213> ORGANISM: Artificial Sequence
<220> FEATURE:
<223> OTHER INFORMATION: Pfk-R primer

<400> SEQUENCE: 85
ccttgattat attaaacatt tgtttataaa cacattgcaa ccccgcggat gaccgcaggg   60
acttaatttg tcccag                                                   76

<210> SEQ ID NO 86
```

<210> SEQ ID NO 86
<211> LENGTH: 76
<212> TYPE: DNA
<213> ORGANISM: Artificial Sequence
<220> FEATURE:
<223> OTHER INFORMATION: glpx-F primer

<400> SEQUENCE: 86

```
ctgggacaaa ttaagtccct gcggtcatcc gcggggttgc aatgtgttta taaacaaatg      60
tttaatataa tcaagg                                                      76
```

<210> SEQ ID NO 87
<211> LENGTH: 83
<212> TYPE: DNA
<213> ORGANISM: Artificial Sequence
<220> FEATURE:
<223> OTHER INFORMATION: glpx-F primer

<400> SEQUENCE: 87

```
actcctccct aactttattt ttttaattac tcattgccgg cttattctac cactaattta      60
cttttattca agtcatgaat agc                                              83
```

<210> SEQ ID NO 88
<211> LENGTH: 100
<212> TYPE: DNA
<213> ORGANISM: Artificial Sequence
<220> FEATURE:
<223> OTHER INFORMATION: rpe-F primer

<400> SEQUENCE: 88

```
ataaaagtaa attagtggta gaataagccg gcataaataa cgacaagcac acagaggagg      60
tagagatgat aaaattggca gcatcaattt tatccgcaga                            100
```

<210> SEQ ID NO 89
<211> LENGTH: 76
<212> TYPE: DNA
<213> ORGANISM: Artificial Sequence
<220> FEATURE:
<223> OTHER INFORMATION: rpe-R primer

<400> SEQUENCE: 89

```
ctcctattga taagtacgat atagaaacta gtctaaatac ttccctttaa taactctata      60
ttttttttga tatcgc                                                      76
```

<210> SEQ ID NO 90
<211> LENGTH: 114
<212> TYPE: DNA
<213> ORGANISM: Artificial Sequence
<220> FEATURE:
<223> OTHER INFORMATION: rpi-F primer

<400> SEQUENCE: 90

```
gtgcaaatgc atattatggt caaaaaacaa agtaaactag tttctatatc gtacttatca      60
ataggaggta cactaaatga agatagcaat aggtagtgat catgcaggat tttc            114
```

<210> SEQ ID NO 91
<211> LENGTH: 136
<212> TYPE: DNA
<213> ORGANISM: Artificial Sequence
<220> FEATURE:
<223> OTHER INFORMATION: rpi-R primer

<400> SEQUENCE: 91

```
ttagcggccg cgaattcgcc cttcccgggt gcttcatgaa gctaatataa tgaagcaaag      60
```

```
actattttac attctttatt ttgctagctt atttcattcc tccattgtat ttttttttcta    120 tttgtgtaat cttgtc                                                     136
```

<210> SEQ ID NO 92
<211> LENGTH: 93
<212> TYPE: DNA
<213> ORGANISM: Artificial Sequence
<220> FEATURE:
<223> OTHER INFORMATION: ngop-F primer

<400> SEQUENCE: 92

```
gccgagaaaa ctattggttg gaatggcgtg tgtgttagcc aaagctcagg cctctcgagt    60
taaaagtagg tgttttgtac ataataatat cag                                  93
```

<210> SEQ ID NO 93
<211> LENGTH: 136
<212> TYPE: DNA
<213> ORGANISM: Artificial Sequence
<220> FEATURE:
<223> OTHER INFORMATION: ngop-R primer

<400> SEQUENCE: 93

```
attattttaa tcaatatatt tgttaaaaa gtacccgggt gcttcatgaa gctaatataa     60
tgaagcaaag actattttac attctttatt ttgctagctt atttcattcc tccattgtat   120 ttttttcta tttgtg                                                    136
```

<210> SEQ ID NO 94
<211> LENGTH: 33
<212> TYPE: DNA
<213> ORGANISM: Artificial Sequence
<220> FEATURE:
<223> OTHER INFORMATION: gapC-1 primer

<400> SEQUENCE: 94

```
aaaaggatcc aggaatgtca gttacaaaag acg                                  33
```

<210> SEQ ID NO 95
<211> LENGTH: 54
<212> TYPE: DNA
<213> ORGANISM: Artificial Sequence
<220> FEATURE:
<223> OTHER INFORMATION: gapC-2 primer

<400> SEQUENCE: 95

```
gggggaggcc taaaaagggg gcattctaac tacctccaaa aatttttttaa tatc           54
```

<210> SEQ ID NO 96
<211> LENGTH: 54
<212> TYPE: DNA
<213> ORGANISM: Artificial Sequence
<220> FEATURE:
<223> OTHER INFORMATION: gapC-3 primer

<400> SEQUENCE: 96

```
cccccttttt aggcctcccc ctagtttaaa gcgctcatta attaatttga atag            54
```

<210> SEQ ID NO 97
<211> LENGTH: 36
<212> TYPE: DNA
<213> ORGANISM: Artificial Sequence
<220> FEATURE:
<223> OTHER INFORMATION: gapC-4 primer

<400> SEQUENCE: 97
aaaaggatcc gagtctttgg tccaatatct aatccc            36

<210> SEQ ID NO 98
<211> LENGTH: 24
<212> TYPE: DNA
<213> ORGANISM: Artificial Sequence
<220> FEATURE:
<223> OTHER INFORMATION: gapC-0 primer

<400> SEQUENCE: 98
ggactatata tgtccagcga ggtg                         24

<210> SEQ ID NO 99
<211> LENGTH: 21
<212> TYPE: DNA
<213> ORGANISM: Artificial Sequence
<220> FEATURE:
<223> OTHER INFORMATION: gapC-5 primer

<400> SEQUENCE: 99
agcagcactg tctcctccac c                            21

<210> SEQ ID NO 100
<211> LENGTH: 24
<212> TYPE: DNA
<213> ORGANISM: Artificial Sequence
<220> FEATURE:
<223> OTHER INFORMATION: gapC-D primer

<400> SEQUENCE: 100
agaaggagct ttcgtagtaa acgg                         24

<210> SEQ ID NO 101
<211> LENGTH: 26
<212> TYPE: DNA
<213> ORGANISM: Artificial Sequence
<220> FEATURE:
<223> OTHER INFORMATION: gapC-R primer

<400> SEQUENCE: 101
gtgtatccaa atgattcatc agcagc                       26

<210> SEQ ID NO 102
<211> LENGTH: 44
<212> TYPE: DNA
<213> ORGANISM: Artificial Sequence
<220> FEATURE:
<223> OTHER INFORMATION: crt-1 primer

<400> SEQUENCE: 102
aaaaggatcc gtaaaaagga tagtgtaatt gaataataat gtgg   44

<210> SEQ ID NO 103
<211> LENGTH: 54
<212> TYPE: DNA
<213> ORGANISM: Artificial Sequence
<220> FEATURE:
<223> OTHER INFORMATION: crt-2 primer

<400> SEQUENCE: 103
gggggaggcc taaaaagggg gcatgactaa tcctcctaaa atatttttt attg   54

<210> SEQ ID NO 104
<211> LENGTH: 59

```
<212> TYPE: DNA
<213> ORGANISM: Artificial Sequence
<220> FEATURE:
<223> OTHER INFORMATION: crt-3 primer

<400> SEQUENCE: 104 ccccctttt aggcctcccc ctaggaggta agtttatatg gattttaatt taacaagag      59

<210> SEQ ID NO 105
<211> LENGTH: 33
<212> TYPE: DNA
<213> ORGANISM: Artificial Sequence
<220> FEATURE:
<223> OTHER INFORMATION: crt--4 primer

<400> SEQUENCE: 105
aaaaggatcc gcatgaagct tagctcttgc agc                                  33

<210> SEQ ID NO 106
<211> LENGTH: 26
<212> TYPE: DNA
<213> ORGANISM: Artificial Sequence
<220> FEATURE:
<223> OTHER INFORMATION: crt-0 primer

<400> SEQUENCE: 106
gtagcttttg cctatatttt tgcagc                                          26

<210> SEQ ID NO 107
<211> LENGTH: 26
<212> TYPE: DNA
<213> ORGANISM: Artificial Sequence
<220> FEATURE:
<223> OTHER INFORMATION: Crt-5 primer

<400> SEQUENCE: 107
caactatatt catcctctta acctcc                                          26

<210> SEQ ID NO 108
<211> LENGTH: 30
<212> TYPE: DNA
<213> ORGANISM: Artificial Sequence
<220> FEATURE:
<223> OTHER INFORMATION: crt-F primer

<400> SEQUENCE: 108
cactaaaaga aatggattat gttataggtg                                      30

<210> SEQ ID NO 109
<211> LENGTH: 27
<212> TYPE: DNA
<213> ORGANISM: Artificial Sequence
<220> FEATURE:
<223> OTHER INFORMATION: crt-R primer

<400> SEQUENCE: 109
gctaaagcag tatcaatatc acactgc                                         27
```

CLOSTRIDIUM ACETOBUTYLICUM STRAINS UNABLE TO PRODUCE HYDROGEN AND USEFUL FOR THE CONTINUOUS PRODUCTION OF CHEMICALS AND FUELS

DOMAIN OF THE INVENTION

The present invention relates to a new strain of *Clostridium acetobutylicum* modified to be unable to produce hydrogen and its use for the continuous production of bulk chemicals such as lactate, 1,3-propanediol, ethanol, butanol, isobutanol, 1,3-butanediol, acetate, acetone, isopropanol, 3-hydroxy-3-methylbutyrate and isobutene at high yield.

BACKGROUND OF THE INVENTION

*Clostridium acetobutylicum* is known for nearly 100 years to produce solvents such as butanol, as well as other bulk chemicals. It was previously shown (B. H. Kim, et al 1984) that the metabolism of *Clostridium acetobutylicum* can be manipulated in favor of n-butanol and ethanol when its [Fe—Fe]-hydrogenase (encoded by the hydA gene) was inhibited by the use of carbon monoxide. In order to use *C. acetobutylicum* to continuously produce compounds like lactate, 1,3-propanediol, ethanol, butanol, isobutanol, 1,3-butanediol, acetate, acetone and isopropanol, 3-hydroxy-3-methylbutyrate, isobutene it would be very useful to inactivate the hydA gene to redirect the electron flux from hydrogen to the production of those chemicals. However, all the attempts to inactivate the hydA gene of *C. acetobutylicum* have been unsuccessful (Cooksley C. M et al, 2012) so far.

The present invention is based on recent finding by the inventors that by simultaneously inactivating the hydA and the thlA genes encoding respectively the main [Fe—Fe]-hydrogenase and the main thiolase, it is possible to get a *C. acetobutylicum* mutant strain unable to produce hydrogen.

BRIEF DESCRIPTION OF THE INVENTION

The present invention concerns a genetically modified *Clostridium acetobutylicum* unable to produce hydrogen, wherein it comprises two attenuated genes, particularly two simultaneously attenuated genes, coding for the main hydrogenase (hydA) and the main thiolase (thlA).

The invention also concerns a method for the preparation of a genetically modified *Clostridium acetobutylicum* unable to produce hydrogen, comprising attenuating, particularly simultaneously attenuating, genes coding for the main hydrogenase (hydA) and the main thiolase (thlA).

The modified *Clostridium acetobutylicum* is also further modified for an improved continuous production of a targeted bulk chemical, by attenuating and/or deleting and/or replacing genes to favor a metabolic pathway for the production of the targeted bulk chemical.

The invention also concerns a method for the production of a targeted bulk chemical from different carbohydrates (C3, C5, C6 and C12), comprising culturing a genetically modified *Clostridium acetobutylicum* of the invention on a culture medium comprising different carbohydrates (C3, C5, C6 and C12) as main source of carbon, and recovering the targeted bulk chemical from the culture medium.

Bulk chemicals susceptible to be continuously produced by culturing *Clostridium acetobutylicum* are selected among the group consisting of lactate, 1,3-propanediol, ethanol, n-butanol, isobutanol, 1, 3-butanediol, acetate, acetone, isopropanol, 3-hydroxy-3-methylbutyrate, isobutene and mixtures thereof.

EMBODIMENTS OF THE INVENTION

In a first embodiment, the present invention concerns a genetically modified *Clostridium acetobutylicum* unable to produce hydrogen In a second embodiment, the invention concerns a genetically modified *Clostridium acetobutylicum* according to the first embodiment, wherein the main [Fe—Fe]-hydrogenase encoding gene (hydA) and the main thiolase encoding gene (thlA) are attenuated.

In a third embodiment, the invention concerns a genetically modified *Clostridium acetobutylicum* according to embodiment 1 or 2, wherein it comprises at least one additional modification to produce lactate as the main product.

In a fourth embodiment, the present invention further concerns a genetically modified *Clostridium acetobutylicum* according to embodiment 3, wherein the at least one additional modification comprises the attenuation of at least one gene involved in the ethanol formation pathways selected in the group comprising adhE1 and adhE2.

In a fifth embodiment, the present invention concerns a genetically modified *Clostridium acetobutylicum* according to embodiment 1 or 2, wherein it comprises at least one additional modification to produce ethanol as the main product.

In a sixth embodiment, the present invention concerns a genetically modified *Clostridium acetobutylicum* according to fifth embodiment, wherein the at least one additional modification to produce ethanol as the main product comprises attenuation of at least one gene involved in the lactate formation pathways selected in the group comprising ldhA, ldhB, ldhC and ldhD.

In a seventh embodiment, the present invention concerns a genetically modified *Clostridium acetobutylicum* according to fifth or sixth embodiment, wherein it comprises at least one additional modification to produce n-butanol as the main product.

In an eighth embodiment, the present invention concerns a genetically modified *Clostridium acetobutylicum* according to seventh embodiment, wherein the at least one additional modification comprises expressing a gene encoding a heterologous thiolase less inhibited by CoASH than ThlA.

In a ninth embodiment, the present invention concerns a genetically modified *Clostridium acetobutylicum* according to eighth embodiment, wherein the gene encoding an heterologous thiolase comprises an optimized synthetic gene encoding the AtoB thiolase from *Escherichia coli*.

In a tenth embodiment, the present invention concerns a genetically modified *Clostridium acetobutylicum* according to any of embodiments seventh to ninth, wherein at least one of the genes ptb and buk encoding the for the final two steps of butyrate formation is attenuated. In particular, the final two steps of butyrate formation comprise the conversion of butyryl-CoA in butyryl-Phosphate by phosphotransbutyrylase and the conversion of butyryl-phosphate in butyrate by butyrate kinase In an eleventh embodiment, the present invention concerns a genetically modified *Clostridium acetobutylicum* according to third embodiment, wherein it comprises at least one additional modification to produce isobutanol as the main product.

In a twelfth embodiment, the present invention concerns a genetically modified *Clostridium acetobutylicum* according to eleventh embodiment, wherein the at least one additional modification to produce isobutanol as the main product comprises the overexpression of at least one gene comprised in the group consisting of homologous acetolactate synthase encoding gene, homologous ketoacid reductoisomerase encoding gene, homologous dihydroxy acid dehydratase encoding gene, homologous ketoacid decarboxylase encoding gene and homologous alcohol dehydrogenase encoding gene.

In a thirteenth embodiment, the present invention concerns a genetically modified *Clostridium acetobutylicum* according to eleventh and twelfth embodiment, wherein the at least one additional modification comprises attenuation of at least one gene involved in the lactate formation pathways which is selected in the group comprising ldhA, ldhB, ldhC and ldhD.

In a fourteenth embodiment, the present invention concerns a genetically modified *Clostridium acetobutylicum* according to third embodiment, wherein it comprises at least one additional modification to convert glycerol to 1, 3 propanediol as the main product.

In a fifteenth embodiment, the present invention concerns a genetically modified *Clostridium acetobutylicum* according to fourteenth embodiment, wherein the at least one additional modification comprises the expression of heterologous genes coding for a B12-independent diol-dehydratase and a 1,3 propanediol dehydrogenase.

In a sixteenth embodiment, the present invention concerns a genetically modified *Clostridium acetobutylicum* according to third embodiment, wherein it comprises at least one additional modification for the production of acetate as the main product.

In a seventeenth embodiment, the present invention concerns a genetically modified *Clostridium acetobutylicum* according to sixteenth embodiment, wherein the at least one additional modification to produce acetate as the main product comprises the overexpression of at least one gene comprised in the group consisting of homologous Fructose bis phosphate phosphatase encoding gene, homologous Ribose-5-phosphate isomerase encoding gene, homologous Ribulose-5-phosphate 3-epimerase encoding gene, homologous Transketolase encoding gene, homologous transaldolase encoding gene and homologous Phosphoketolase encoding gene.

In an eighteenth embodiment, the present invention concerns a genetically modified *Clostridium acetobutylicum* according to sixteenth or seventeenth embodiment, wherein the at least one additional modification to produce acetate as the main product comprises the attenuation of at least one gene comprised in the group consisting of PhosphoFructokinase encoding genes, Glucose PTS encoding gene and NAD+ dependent Glyceraldehyde-3-Phosphate dehydrogenase encoding gene.

In a nineteenth embodiment, the present invention concerns a genetically modified *Clostridium acetobutylicum* according to seventeenth embodiment, wherein it comprises at least one further additional modification for the production of acetone as the main product.

In a twentieth embodiment, the present invention concerns a genetically modified *Clostridium acetobutylicum* according to eighteenth embodiment, wherein it comprises at least one further additional modification for the production of isopropanol as the main product.

In a twentyfirst embodiment, the present invention concerns a genetically modified *Clostridium acetobutylicum* according to eighteenth embodiment, wherein it comprises at least one further additional modification for the production of 3-hydro-3-methylbutyrate as the main product.

In a twentysecond embodiment, the present invention concerns a genetically modified *Clostridium acetobutylicum* according to the twentieth embodiment, wherein it comprises at least one additional modification for the production of isobutene as the main product.

In a twentythird embodiment, the present invention concerns a genetically modified *Clostridium acetobutylicum* according to any of the seventh to tenth embodiments, wherein it comprises at least one additional modification for the production of 1, 3 butanediol as the main product.

DETAILED DESCRIPTION OF THE INVENTION

As used herein the following terms may be used for interpretation of the claims and specification.

The name "*Clostridium acetobutylicum*" is known in the art and means strain producing acetone butanol and ethanol (Tamaru, Y. et al., 1979) and possessing a megaplasmid carrying the solvent forming genes (Nolling et al., 2001). Preferred strains of *Clostridium acetobutylicum* used in the present invention are strains known to be used and modified for the production of solvents and other bulk chemicals, such as *Clostridium acetobutylicum* ATCC 824, *Clostridium acetobutylicum* DSM 1731 and *Clostridium acetobutylicum* ATCC 4259.

The term "bulk chemical(s)" means large volume chemicals. Preferred bulk chemical susceptible to be produced with the strain of the invention are selected among the group consisting of lactate, 1,3-propanediol, ethanol, n-butanol, isobutanol, 1,3-butanediol, acetate, acetone, isopropanol, 3-hydroxy-3-methylbutyrate, isobutene and mixtures thereof.

The expression "appropriate culture medium" refers to a culture medium adapted for the used microorganism as it is well known by the man skilled in the art.

The term "carbon substrate" or "source of carbon" means any carbon source capable of being metabolized by a microorganism wherein the substrate contains at least one carbon atom. In particular it may be glucose, sucrose, mono- or oligosaccharides, starch or its derivatives, glycerol, and their mixtures thereof.

The term "attenuation" refers to a decreased expression of a gene or a decreased activity of the protein, product of the gene. The man skilled in the art knows numerous means to obtain this result, and for example:

Introduction of a mutation into the gene, decreasing the expression level of this gene, or the level of activity of the encoded protein.

Replacement of the natural promoter of the gene by a low strength promoter, resulting in a lower expression Use of elements destabilizing the corresponding messenger RNA or the protein Deletion of the gene if no expression is needed.

The term "deleted gene" means that a substantial part of the coding sequences of said gene was removed. Preferably, at least 50% of the coding sequence was removed, and more preferably at least 80%.

In the context of the present invention, the term "main" used in conjunction with gene means that while other gene coding for the same activity are present but the said gene is the gene that is necessary and sufficient by itself to cause the expression of the associated protein and/or of the phenotype, i.e. the enzymatic activity.

In the context of the present invention, the term 'main" used in conjunction with a product or metabolite, means that the said product or metabolite is produced or expressed preferentially by the microorganism in a quantity that is by far in excess compared to other products or metabolites produced by the said microorganism.

In the context of the present invention, the term "curing" used in conjunction with a megaplasmid, means the elimination of the said megaplasmid from the cell of the microorganism containing by appropriate means that are, for example, able to inhibit plasmid replication but sufficient to maintain chromosome replication.

In the context of the present invention, the term "overexpression of a gene" means that the quantity of the protein (i.e. enzyme) encoded by the gene is greater than the situation in a control microorganism that does not comprise a modification which is responsible for the said "overexpression". An overexpression of a gene may also be the result of the production of the same quantity of protein but of which the specific activity is enhanced thanks to the modification. Eventually an overexpression may be the result of both increase in quantity of a protein as well as increase in specific activity of said protein.

In the description of the present invention, enzymes are identified by their specific activities. This definition thus includes all polypeptides that have the defined specific activity also present in other organisms, more particularly in other microorganisms. Often enzymes with similar activities can be identified by their grouping to certain families defined as PFAM or COG.

PFAM (protein families' database of alignments and hidden Markov models; worldwide web address: sanger. ac.uk/Software/Pfam/) represents a large collection of protein sequence alignments. Each PFAM makes it possible to visualize multiple alignments, see protein domains, evaluate distribution among organisms, gain access to other databases, and visualize known protein structures.

COGs (clusters of orthologous groups of proteins; worldwide web address: ncbi.nlm.nih.gov/COG/) are obtained by comparing protein sequences from 43 fully sequenced genomes representing 30 major phylogenic lines. Each COG is defined from at least three lines, which permits the identification of former conserved domains.

The means of identifying homologous sequences and their percentage homologies are well known to those skilled in the art, and include in particular the BLAST programs, which can be used from the website worldwide web address: ncbi.nlm.nih.gov/BLAST/ with the default parameters indicated on that website. The sequences obtained can then be exploited (e.g., aligned) using, for example, the programs CLUSTALW (worldwide web address: ebi.ac.uk/clustalw/) or MULTALIN (worldwide web address: prodes.toulouse.inra.fr/multalin cgi-bin/multalin.pl), with the default parameters indicated on those websites.

Using the references given on GenBank for known genes, those skilled in the art are able to determine the equivalent genes in other organisms, bacterial strains, yeasts, fungi, mammals, plants, etc. This routine work is advantageously done using consensus sequences that can be determined by carrying out sequence alignments with genes derived from other microorganisms, and designing degenerate probes to clone the corresponding gene in another organism. These routine methods of molecular biology are well known to those skilled in the art, and are described, for example, in Sambrook et al. (Molecular Cloning: a Laboratory Manual. 2nd ed. Cold Spring Harbor Lab., Cold Spring Harbor, N.Y., 1989.).

In a first embodiment, the present invention concerns a genetically modified *Clostridium acetobutylicum* unable to produce hydrogen.

In a second embodiment, the invention concerns a genetically modified *Clostridium acetobutylicum* according to the first embodiment, wherein the main [Fe—Fe]-hydrogenase encoding gene (hydA) and the main thiolase encoding gene (thlA) are attenuated.

The present invention is also related to a genetically modified *Clostridium acetobutylicum* unable to produce hydrogen by, particularly simultaneously, attenuating genes coding for the main hydrogenase (hydA) and the main thiolase (thlA). Such attenuation, particularly simultaneous attenuation, of both genes can be done in two steps (FIG. 1):

First the integration of two non-replicative plasmids that each carry i) a markerless deletion cassette comprising two sequences homologous to selected regions around the DNA sequence to delete, allowing the integration of the non replicative plasmid, ii) an antibiotic resistance marker and iii) a counter-selectable marker that can be used as a positive selection for the second recombination events and the loss of the integrated plasmids Second use of the counter-selectable marker to select for the second recombination event that will lead to the simultaneous gene deletion and the loss of the integrated plasmids.

A counter-selectable marker is a gene whose presence is lethal to the host organism under certain circumstances such as the presence of its cognate substrate. Counter-selectable markers can be used as a positive selection for the loss of the plasmids.

Preferentially the counter-selectable marker gene is a gene that restores the activity of an absent or deleted non-essential endogenous gene. Counterselectable markers that can also be used in clostridia include gene giving sensitivity to 5-fluoro-uracile (5-FU), gamma-glutamyl hydrazide (GBS) or 8-aza-2,6-diaminopurine (8ADP). In a preferred embodiment, the counter-selectable marker is the upp gene, which encodes uracil phosphoribosyl-transferase that promotes transformation of 5-fluoro-uracile (5-FU) to a toxic product. Cells having Upp activity cannot grow on a 5-FU medium.

The present invention also provides for a genetically modified *Clostridium acetobutylicum* unable to produce hydrogen which is further modified to produce lactate, ethanol, 1,3-propanediol, n-butanol, isobutanol, 1, 3-butanediol, acetate, acetone, isopropanol, 3-hydroxy-3-methylbutyrate, isobutene.

In another specific embodiment of the invention, modifications for the continuous production of lactate are introduced into the genetically modified *Clostridium acetobutylicum* unable to produce hydrogen.

In a third embodiment, the invention concerns a genetically modified *Clostridium acetobutylicum* according to embodiment 1 or 2, wherein it comprises at least one additional modification to produce lactate as the main product.

One modification can be the attenuation of genes involved in ethanol formation pathways.

Preferentially, in the microorganism according to the invention, genes encoding enzyme activities involved in ethanol formation pathways are attenuated in order to increase the yield of lactate:

The adhE1 gene (CAP0162) encoding a bifunctional aldehyde-alcohol dehydrogenase AdhE1 (E.C. 1.2.1.57/1.1.1.-) responsible for the synthesis of ethanol and n-butanol during solventogenic conditions.

The adhE2 gene (CAP0035) encoding a bifunctional aldehyde-alcohol dehydrogenase AdhE2 (E.C. 1.2.1.57/1.1.1.-) responsible for the synthesis of ethanol and butanol during alcohologenic conditions.

In a fourth embodiment, the present invention further concerns a genetically modified *Clostridium acetobutylicum* according to embodiment 3, wherein the at least one additional modification comprises attenuation of at least one gene involved in the ethanol formation pathways selected in the group comprising adhE1 and adhE2 The elimination of ethanol production can be obtained by the attenuation of at least one of these genes. Preferentially the elimination of ethanol production can be obtained by curing the pSOL1 megaplasmid that carries both adhE1 and adhE2.

In a specific embodiment of the invention, modifications for the production of ethanol, particularly the continuous production of ethanol, are introduced into the genetically modified *Clostridium acetobutylicum* unable to produce hydrogen.

In a fifth embodiment, the present invention concerns a genetically modified *Clostridium acetobutylicum* according to embodiment 1 or 2, wherein it comprises at least one additional modification to produce ethanol as the main product.

In a sixth embodiment, the present invention concerns a genetically modified *Clostridium acetobutylicum* according to fifth embodiment, wherein the at least one additional modification to produce ethanol as the main product comprises attenuation of at least one gene involved in the lactate formation pathways selected in the group comprising ldhA, ldhB, ldhC and ldhD.

Preferentially, in the microorganism according to the invention, some genes encoding enzyme activities involved in lactate formation pathways are attenuated in order to increase the yield of ethanol:

The ldhA (CAC0267) and ldhB (CAC3552) genes encoding L-lactate dehydrogenase (E.C. 1.1.1.27) activities, responsible for the synthesis of L-lactate from pyruvate.

The ldhC (CAC1543) and ldhD (CAC2691) genes encoding D-lactate dehydrogenase (E.C. 1.1.1.28) activities, responsible for the synthesis of D-lactate from pyruvate.

Preferentially, the elimination of lactate production can be obtained by the attenuation of at least one of these genes.

In another specific embodiment of the invention, modifications for the continuous production of n-butanol are introduced into the genetically modified *Clostridium acetobutylicum* unable to produce hydrogen and producing ethanol as the main product.

In a seventh embodiment, the present invention concerns a genetically modified *Clostridium acetobutylicum* according to fifth or sixth embodiment, wherein it comprises at least one additional modification to produce n-butanol as the main product.

In an eighth embodiment, the present invention concerns a genetically modified *Clostridium acetobutylicum* according to seventh embodiment, wherein the at least one additional modification comprises expressing a gene encoding a heterologous thiolase less inhibited by CoASH than ThlA.

In a ninth embodiment, the present invention concerns a genetically modified *Clostridium acetobutylicum* according to eighth embodiment, wherein the gene encoding an heterologous thiolase comprises an optimized synthetic gene encoding the AtoB thiolase from *Escherichia coli*.

Preferentially, in the microorganism according to the invention, the thiolase (E.C. 2.3.1.9) activity can be restored using a thiolase enzyme at least 10 times less sensitive to CoASH than ThlA. The preferred method uses AtoB from *Escherichia coli* expressed from a codon harmonize synthetic atoB gene.

In a tenth embodiment, the present invention concerns a genetically modified *Clostridium acetobutylicum* according to any of embodiments seventh to ninth, wherein the at least one of the genes ptb and buk encoding the final two steps of butyrate formation is attenuated. Particularly the two genes are attenuated. In particular, the final two steps of butyrate formation comprise the conversion of butyryl-CoA in butyryl-Phosphate by phosphotransbutyrylase and the conversion of butyryl-phosphate in butyrate by butyrate kinase Preferentially, in the microorganism according to the invention, some enzyme activities involved in the butyrate formation pathway are attenuated in order to increase the yield of n-butanol: phosphotransbutyrylase activity (E.C. 2.3.1.19) encoded by ptb (CAC3076) and butyrate kinase (E.C. 2.7.2.7) activities encoded by buk (CAC3076) and CAC1660. Preferentially the elimination of butyrate formation can be obtained by the attenuation of at least one of these genes.

In another specific embodiment of the invention, modifications for the continuous production of isobutanol are introduced into the genetically modified *Clostridium acetobutylicum* unable to produce hydrogen and producing lactate as the main product.

In an eleventh embodiment, the present invention concerns a genetically modified *Clostridium acetobutylicum* according to third embodiment, wherein it comprises at least one additional modification to produce isobutanol as the main product.

In a twelfth embodiment, the present invention concerns a genetically modified *Clostridium acetobutylicum* according to eleventh embodiment, wherein the at least one additional modification to produce isobutanol as the main product comprises the overexpression of at least one gene comprised in the group consisting of homologous acetolactate synthase encoding gene, homologous ketoacid reductoisomerase encoding gene, homologous dihydroxy acid dehydratase encoding gene, homologous ketoacid decarboxylase encoding gene and homologous alcohol dehydrogenase encoding gene.

Preferentially, in the microorganism according to the invention, expression of some homologous genes encoding enzyme activities involved in the isobutanol formation pathway is increased:

alsS (CAC3652), ilvB (CAC3169) and ilvN (CAC3176) encoding acetolactate synthase (E.C. 2.2.1.6) activities.

ilvC (CAC0091), CAC1605 and CAC2937 encoding keto-acid reductoisomerase (E.C. 1.1.1.86) activities.

ilvD1 (CAC3170) and ilvD2 (CAC3604) encoding dihydroxyacid dehydratase (E.C. 4.2.1.9) activities.

pdc (CAP0025) encoding keto-acid decarboxylase (E.C. 4.1.1.1) activity bdhA (CAC3299), bdhB (CAC3298) or bdhC (CAC3392) encoding alcohol dehydrogenase (E.C. 1.1.1.-) activities.

Preferentially, the isobutanol production can be obtained by the overexpression of at least one of these genes.

In a thirteenth embodiment, the present invention concerns a genetically modified *Clostridium acetobutylicum* according to eleventh and twelfth embodiment, wherein the at least one additional modification comprises attenuation of at least one gene involved in the lactate formation pathways selected in the group comprising ldhA, ldhB, ldhC and ldhD.

Preferentially, in the microorganism according to the invention, some genes encoding enzyme activities involved in lactate formation pathways are attenuated in order to increase the yield of isobutanol:

The ldhA (CAC0267) and ldhB (CAC3552) genes encoding L-lactate dehydrogenase (E.C. 1.1.1.27) activities, responsible for the synthesis of L-lactate from pyruvate.

The ldhC (CAC1543) and ldhD (CAC2691) genes encoding D-lactate dehydrogenase (E.C. 1.1.1.28) activities, responsible for the synthesis of D-lactate from pyruvate.

Preferentially, the elimination of lactate production can be obtained by the attenuation of at least one of these genes.

In another specific embodiment of the invention, modifications for the continuous production of 1, 3 propanediol from glycerol are introduced into the genetically modified Clostridium acetobutylicum unable to produce hydrogen and producing lactate as the main product.

In a fourteenth embodiment, the present invention concerns a genetically modified Clostridium acetobutylicum according to third embodiment, wherein it comprises at least one additional modification to convert glycerol to 1, 3 propanediol as the main product.

In a fifteenth embodiment, the present invention concerns a genetically modified Clostridium acetobutylicum according to fourteenth embodiment, wherein the at least one additional modification comprises the expression of heterologous genes coding for a B12-independent diol-dehydratase and a 1,3 propanediol dehydrogenase Preferentially, the B12-independent glycerol dehydratase (E.C. 4.2.1.30) and the NAD+ dependent 1, 3 propanediol dehydrogenase (E.C. 1.1.1.202) activities are increased. The preferred method is the overexpression of the dhaB1, dhaB2 genes coding for glycerol dehydratase and glycerol dehydratase activating enzyme, and dhaT gene coding for NAD+ dependant 1, 3 propanediol dehydrogenase from Clostridium butyricum (Raynaud et al,). Additionally, NAD+ dependant 1, 3 propanediol dehydrogenase can be replaced by an NADP+ dependant 1, 3 propanediol dehydrogenase (E.C. 1.1.1-) encoded by bdhB (CAC3298) or bdhA (CAC3299).

In one embodiment, the present invention concerns a genetically modified Clostridium acetobutylicum according to fourteenth and fifteenth embodiments, wherein the at least one additional modification comprises attenuation of at least one gene involved in the lactate formation pathway selected in the group comprising ldhA, ldhB, ldhC and ldhD.

Preferentially, in the microorganism according to the invention, some genes encoding enzyme activities involved in lactate formation pathways are attenuated in order to increase the yield of 1,3 propanediol:

The ldhA (CAC0267) and ldhB (CAC3552) genes encoding L-lactate dehydrogenase (E.C. 1.1.1.27) activities, responsible for the synthesis of L-lactate from pyruvate.

The ldhC (CAC1543) and ldhD (CAC2691) genes encoding D-lactate dehydrogenase (E.C. 1.1.1.28) activities, responsible for the synthesis of D-lactate from pyruvate.

Preferentially, the elimination of lactate production can be obtained by the attenuation of at least one of these genes.

In another specific embodiment of the invention, modifications for the continuous production of acetate are introduced into the genetically modified Clostridium acetobutylicum unable to produce hydrogen and producing lactate as the main product.

In a sixteenth embodiment, the present invention concerns a genetically modified Clostridium acetobutylicum according to third embodiment, wherein it comprises at least one additional modification for the production of acetate as the main product.

In a seventeenth embodiment, the present invention concerns a genetically modified Clostridium acetobutylicum according to sixteenth embodiment, wherein the at least one additional modification to produce acetate as the main product comprises the overexpression of at least one gene comprised in the group consisting of homologous Fructose bis phosphate phosphatase encoding gene, homologous Ribose-5-phosphate isomerase encoding gene, homologous Ribulose-5-phosphate 3-epimerase encoding gene, homologous Transketolase encoding gene, homologous Transaldolase encoding gene and homologous Phosphoketolase encoding gene.

In an eighteenth embodiment, the present invention concerns a genetically modified Clostridium acetobutylicum according to sixteenth or seventeenth embodiment, wherein the at least one additional modification to produce acetate as the main product comprises the attenuation of at least one gene comprised in the group consisting of PhosphoFructokinase encoding gene, Glucose PTS encoding gene and NAD+ dependent Glyceraldehyde-3-Phosphate dehydrogenase encoding gene.

Accordingly, preferentially, in the microorganism according to the invention, at least one enzyme activity involved in a non oxidative glycolytic pathway are increased and are selected in the group comprising:

Fructose bis phosphate phosphatase (E.C. 3.1.3.11) activities encoded by glpX (CAC1088) and CAC1572.

Ribose-5-phosphate isomerase (E.C. 5.3.1.6) activities encoded by rpiA (CAC1431), rpiB (CAC2880) and rpiC (CAC0726)

Ribulose-5-phosphate 3-epimerase (E.C. 5.1.3.1) activity encoded by rpe (CAC1730)

Transketolase (E.C. 2.2.1.1) activities encoded by tkt (CAC0944) and (CAC1348).

Transaldolase (E.C. 2.2.1.2) activity encoded by tal (CAC1347)

Phosphoketolase (E.C. 4.1.2.9) activities encoded by xfp (CAC1343)

In one embodiment, the acetate production can be obtained by the overexpression of at least one of these genes.

In one embodiment, in the microorganism according to the invention, at least one enzyme activity competing with the non oxidative glycolytic pathway is decreased and is selected in the group consisting of:

PhosphoFructokinase (E.C. 2.7.1.11) activities encoded by pfk (CAC0517) and lacC (CAC2951)

Glucose transporter (E.C. 2.7.1.69) of the glucose PTS system encoded by CAC0570.

NAD+ dependent Glyceraldehyde-3-Phosphate dehydrogenase (E.C. 1.2.1.12) activity encoded by gapC (CAC0709)

Preferentially, the decrease of activity can be obtained by the attenuation of at least one of these genes.

Preferentially, for the conversion of glucose to acetate at high yield, a non PTS glucose transporter like GlcP (glucose/H+ symporter) encoded by the glcP (BSU10520) gene of Bacillus subtilis or the glcP (SEVCU071_1542) gene of Saphylococcus epidermidis is expressed to replace the glucose PTS and develop a PEP independent glucose transport system (transport of glucose in symport with a proton).

In another specific embodiment of the invention, modifications are introduced for the continuous production of acetone into the genetically modified *Clostridium acetobutylicum* unable to produce hydrogen and producing acetate as the main product.

In a nineteenth embodiment, the present invention concerns a genetically modified *Clostridium acetobutylicum* according to eighteenth embodiment, wherein it comprises at least one further additional modification for the production of acetone as the main product.

Preferentially, in the microorganism according to the invention, at least one homologous enzyme activity involved in the acetone pathway is increased and is selected in the group consisting of:

Acetate-acetoacetate CoA-transferase (E.C. 2.8.3.-) encoded by ctfA (CAP0163) and ctfB (CAP0164)
Acetoacetate decarboxylase (E.C. 4.1.1.4) encoded by adc (CAP0165)

In one embodiment, the acetone production can be obtained by the overexpression of at least one of these genes.

In one embodiment, in the microorganism according to the invention, the thiolase activity can be restored using a thiolase enzyme at least 10 times less sensitive to CoASH than ThlA. The preferred method use AtoB from *Escherichia coli* expressed from a codon harmonize synthetic atoB gene.

In another specific embodiment of the invention, modifications are introduced for the continuous production of isopropanol into the genetically modified *Clostridium acetobutylicum* unable to produce hydrogen and producing acetone as the main product.

In a twentieth embodiment, the present invention concerns a genetically modified *Clostridium acetobutylicum* according to eighteenth embodiment, wherein it comprises at least one further additional modification for the production of isopropanol as the main product.

Preferentially, in the microorganism according to the invention, a heterologous enzyme activity involved in acetone reduction to isopropanol is introduced: secondary alcohol dehydrogenase from *Clostridium beijerinckii* B593 encoded by sadh (accession number AAA23199).

In another specific embodiment of the invention, modifications are introduced for the continuous production of 3-hydroxy-3-methylbutyrate into the genetically modified *Clostridium acetobutylicum* unable to produce hydrogen and producing acetone as the main product.

In a twentyfirst embodiment, the present invention concerns a genetically modified *Clostridium acetobutylicum* according to eighteenth embodiment, wherein it comprises at least one further additional modification for the production of 3-hydro-3-methylbutyrate as the main product Preferentially, in the microorganism according to the invention, a heterologous enzyme activity involved in acetyl-CoA plus acetone conversion to 3-hydroxy-3-methylbutyrate is introduced: HMG-CoA synthase (E.C. 2.3.3.10) or HMG-CoA lyase (E.C. 4.1.3.4).

In another specific embodiment of the invention, modifications are introduced for the continuous production of isobutene into the genetically modified *Clostridium acetobutylicum* unable to produce hydrogen and producing 3-hydroxy-3-methylbutyrate as the main product. In a twentysecond embodiment, the present invention concerns a genetically modified *Clostridium acetobutylicum* according to the twentieth embodiment, wherein it comprises at least one additional modification for the production of isobutene as the main product.

Preferentially, in the microorganism according to the invention, an heterologous enzyme activity involved in 3-hydroxy-3-methylbutyrate conversion to isobutene is introduced: Mevalonate diphosphate decarboxylase (E.C. 4.1.1.33)

In another specific embodiment of the invention, modifications for the continuous production of 1, 3 butanediol are introduced into the genetically modified *Clostridium acetobutylicum* unable to produce hydrogen and producing n-butanol as the main product.

In a twentythird embodiment, the present invention concerns a genetically modified *Clostridium acetobutylicum* according to any of the seventh to tenth embodiments, wherein it comprises at least one additional modification for the production of 1, 3 butanediol as the main product.

Preferentially the adhE2 (CAC035) gene can be replaced by an evolved adhE2 gene (adhE2*) coding for an AdhE2 enzyme that converts S-3-hydroxybutyryl-CoA to 1, 3 butanediol.

Preferentially, in the microorganism according to the invention, at least one homologous enzyme activity involved in a non oxidative glycolytic pathway is increased and selected in the group consisting of:

Fructose bis phosphate phosphatase (E.C. 3.1.3.11) activities encoded by glpX (CAC1088) and CAC1572.
Ribose-5-phosphate isomerase (E.C. 5.3.1.6) activities encoded by rpiA (CAC1431), rpiB (CAC2880) and rpiC (CAC0726)
Ribulose-5-phosphate 3-epimerase (E.C. 5.1.3.1) activity encoded by rpe (CAC1730)
Transketolase (E.C. 2.2.1.1) activities encoded by tkt (CAC0944) and (CAC1348).
Transaldolase (E.C. 2.2.1.2) activity encoded by tal (CAC1347)
Phosphoketolase (E.C. 4.1.2.9) activities encoded by xfp (CAC1343)

Preferentially, increase flux in the non oxidative glycolytic pathway can be obtained by the overexpression of at least one of these genes.

Preferentially, in the microorganism according to the invention, at least one homologous enzyme activity competing with the non oxidative glycolytic pathway or the 1, 3 butanediol pathway are decreased and is selected in the group consisting of:

PhosphoFructokinase (E.C. 2.7.1.11) activities encoded by pfk (CAC0517) and lacC (CAC2951)
NAD+ dependent Glyceraldehyde-3-Phosphate dehydrogenase (E.C. 1.2.1.12) activity encoded by gapC (CAC0709)
Crotonase (E.C. 4.2.1.17) activity encoded by crt (CAC2712)
The bifunctional aldehyde-alcohol dehydrogenase AdhE1 (E.C. 1.2.1.57/1.1.1.-) responsible for the synthesis of ethanol and n-butanol during solventogenic conditions encoded by the adhE1 gene (CAP0162).
Acetate-acetoacetate CoA-transferase (E.C. 2.8.3.-) encoded by ctfA (CAP0163) and ctfB (CAP0164)

Preferentially, the decrease of activity can be obtained by the attenuation of at least one of these genes.

EXAMPLES

Example 1: Simulation of Performances for the Continuous Production of Lactate, Ethanol, n-Butanol, Isobutanol, 1, 3 Propanediol, 1, 3 Butanediol, Acetone and Isopropanol 1—Parameters for Simulation Simulations have been performed using a recently developed Genome Scale Model (Yoo M, 2014) of *Clostridium acetobutylicum*. The parameters were a phosphate (0.75 mM Phosphate in the fed) and carbon (1000 mM Carbon in the fed) limited chemostat culture run at a dilution rate of 0.05 in synthetic medium. All the simulations were done considering that no hydrogen was produced. To maximize the performances for the production of 1, 3 Butanediol, Acetone and Isopropanol, an Homologous Non Oxidative Glycolytic Pathway (HNOGP) was introduced in the simulations.

2—Simulation Results

Example 2: Construction of Vectors and Strains for the Genetic Engineering of *Clostridium acetobutylicum*

1—Construction of pCatUpp

This plasmid contains a colE1 origin of replication functional in *Escherichia coli*, a catP gene conferring resistance to thiamphenicol and chloramphenicol, the upp gene (encoding the uracil phosphoribosyl-transferase of *C. acetobutylicum*) and a unique BamHI site for the cloning of the replacement cassette. This plasmid was constructed by PCR (Phusion) amplification of a 2845 bp fragment on the pCons::UPP plasmid DNA using oligonucleotides pcat-Upp-F and BamHI-pCat-Upp-R. This fragment was digested by BamHI and ligated. The pcatUpp plasmid (2829 bp) was obtained.

Figure 1:
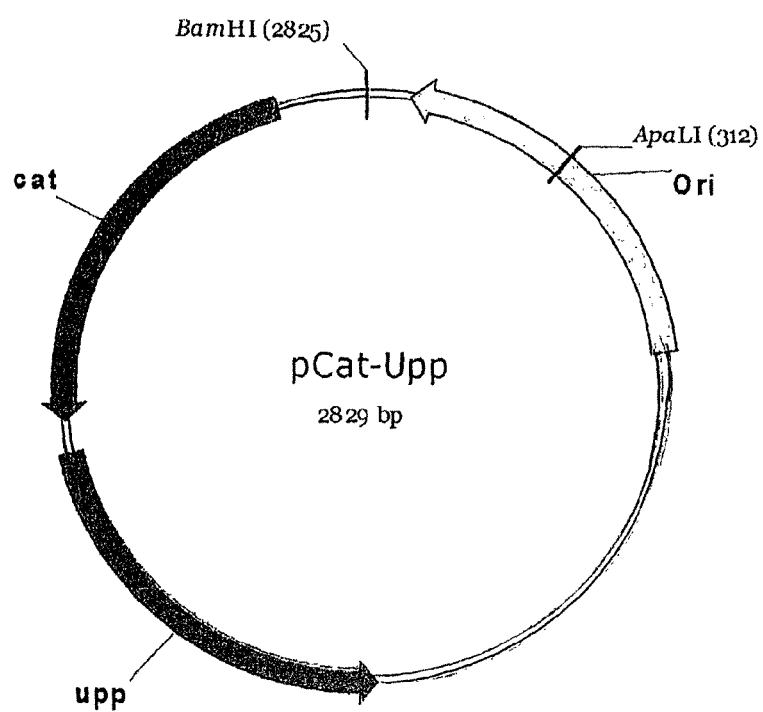
FIG. 1: Map of pCatUpp

The map of pCatUpp is given in FIG. 1.

| Name | SEQ ID No | Primer sequences |
|---|---|---|
| pcat-Upp-F | 1 | AAAAAAGGATCCCTTTTTCGGCAAGTG TTCAAGAAGTTATTAA |
| pcat-Upp-R | 2 | AAAAAAGGATCCGTGAGCAAAAGGCCA GCAAAAGGCC |

2—Construction of the pEryUpp

This plasmid contains a p15A origin of replication functional in *Escherichia coli*, an mlsR gene conferring resistance to erythromycin, a upp gene and a unique BamHI site for the cloning of the replacement cassette. This plasmid was constructed in five steps 1) PCR (Phusion) amplification of the P15A replication origin (P15A fragment) on the plasmid pACYC177, with the primers p15A-F and p15A-R:

2) PCR (Phusion) amplification of the EryR cassette (EryUpp fragment) on the pSOS95-Upp plasmid with the primers eryUpp-F and eryUpp-R 3) PCR (Phusion) amplification of the adhE2 terminator (Teradhe2 fragment) on *Clostridium acetobutylicum* genomic DNA with the primers upp-Teradhe2-F and teradhe2-R.

4) PCR fusion (Phusion) of the "EryUpp" and "Term-B" fragments using the primers eryUpp-F and termadhe2-R to get the "EryUpp-Teradhe2" fragment.

5) Digestion by BamHI and SalI of the "P15A" with "EryUpp-Teradhe2" fragments and ligation to get the pEryUpp plasmid (2582 bp).

| | Lactate | Ethanol | nButanol | Isobutanol | 1,3Propanediol | 1,3Butanediol | Acetone | Isopropanol |
|---|---|---|---|---|---|---|---|---|
| Titer (g/l) | 28.5 | 14.7 | 11.8 | 11.8 | 18.1 | 15.5 | 13.9 | 12.8 |
| Productivity (g · l$^{-1}$ · h$^{-1}$) | 1.43 | 0.73 | 0.59 | 0.59 | 0.90 | 0.78 | 0.70 | 0.64 |
| Yield (g/g) | 0.95 | 0.49 | 0.39 | 0.39 | 0.6 | 0.52 | 0.46 | 0.43 |
| HNOGP | No | No | No | No | No | Yes | Yes | Yes |
| Substrate | Glucose | Glucose | Glucose | Glucose | Glycerol | Glucose | Glucose | Glucose |

Figure 2:
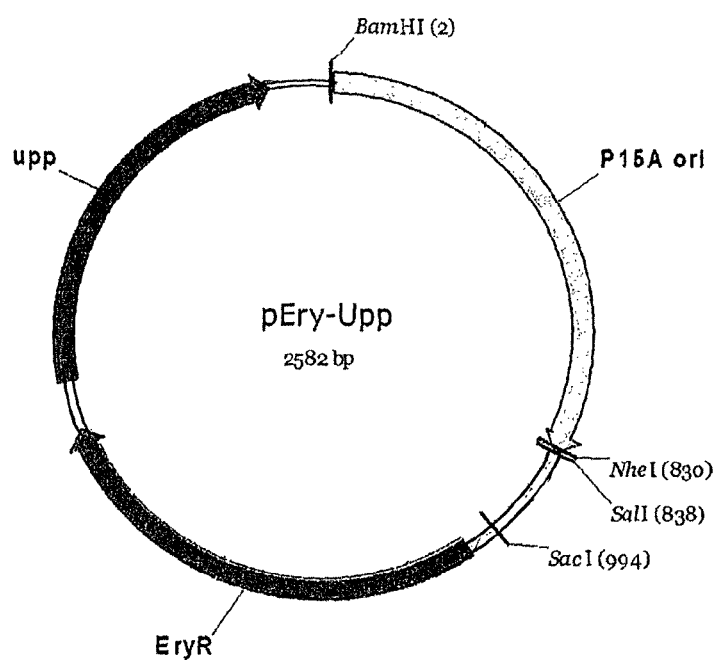
FIG. 2: Map of pEryUpp

The map of pEryUpp is given in FIG. 2.

| Name | SEQ ID No | Primer sequences |
|---|---|---|
| p15A-F | 3 | AAAAGGATCCTTAATAAGATGATCTTCTTGAGATCGTTTTGGT |
| p15A-R | 4 | AAAAGTCGACGCGCTAGCGGAGTGTATACTGGCTTA |
| eryUpp-F | 5 | AAAAGTCGACTCTACGACCAAAAGTATAAAACCTTTAAGAACTTTC |
| eryUpp-R | 6 | TATTTTACATTCTTTATTTTTATTTTGTACCGAATAATCTATCTCCAGCATC |
| upp-Teradhe2-F | 7 | GATTATTCGGTACAAAATAAAAAATAAAGAATGTAAAATAGTCTTTGCTTCATTATATTAGC |
| teradhe2-R | 8 | AAAAGGATCCAAGATAAAAAACAAGAGTAAAATGTAAAATAGTCTATGTGC |

3—Markerless Deletion of the Upp Gene Encoding the Uracil Phosphoribosyl-Transferase in *Clostridium acetobutylicum*

Two DNA fragments surrounding upp (CAC2879) were PCR amplified with the Phusion DNA polymerase with total DNA from *C. acetobutylicum* as template and two specific couples of olignonucleotides as primers. With the couples of primers upp-1-upp-2 and upp-3-upp-4, 1103 bp and 1105 bp DNA fragments were respectively obtained. Primers upp-1 and upp-4 introduce respectively a NaeI and a HpAI site while primers upp-2 and upp-"3 have a complementary 5' extended sequences which introduce a StuI site. DNA fragments upp-1-upp-2 and upp-3-upp-4 were joined in a PCR fusion experiment with primers upp-1 and upp-4 and the resulting fragment was cloned in pCR4-TOPO-Blunt to yield pTOPO:upp. The Upp replacement cassette obtained after NaeI-HpAI double digestion of the pTOPO:upp plasmid was cloned into pCatUpp digested by the same enzymes to yield the pCatΔupp plasmid.

The pCatΔupp plasmid was methylated in vivo and used to transform by electroporation *C. acetobutylicum*. After selection on Petri plates for clones having inserted the pCatΔupp plasmid by homologous recombination (resistant to Thiamphenicol 20 μg/ml), two colonies were further cultured for 24 hours in liquid MS Glucose medium and then subcultured in liquid 2YTG medium without antibiotic. Appropriate dilutions were plated on RCA with 5-FU at 400 μM. Clones resistant to 5-FU were further replica plated on both RCA+5FU and RCA with thiamphenicol at 40 μg/ml. Clones resistant to 5-FU and sensitive to thiamphenicol were further purified on plate with 5-FU and checked by PCR analysis on colonies (with primers upp-0 and upp-5 located outside of the upp replacement cassette and primers upp-F and upp-R located inside of upp) for markerless deletion of upp. The markerless *C. acetobutylicum*Δupp strain was isolated.

| Name | SEQ ID No | Primer sequences |
|---|---|---|
| upp-1 | 9 | AAAAGCCGGCTCCTGATCTATTAATTCTTGATGAACCC |
| upp-2 | 10 | GGGGAGGCCTAAAAAGGGGGATTGCATAAATAAAAAGGGCTGAAAAATAAATTTCAG |
| upp-3 | 11 | CCCCCTTTTTAGGCCTCCCCTTATTTCATTCCTCCATTGTATTTTTTTTCTATTTG |
| upp-4 | 12 | AAAAGTTAACGCTATTATGAATAGGTTAAATAAGTCAGCTGG |
| upp-0 | 13 | AATACAAGCAAAGAGAATAGGCTATGTGCC |
| upp-5 | 14 | AATACAAGCAAAGAGAATAGGCTATGTGCC |
| upp-F | 15 | GGCATATGAAGTAACAAGAGAAATGCAGC |
| upp-R | 16 | ATZZTCTATCTCCAGCATCTCCAAGACC |

4—Markerless Deletion of the CAC1502 Gene Encoding Cac824I the Main Restriction Enzyme in *Clostridium acetobutylicum*

Two DNA fragments surrounding the Cac824I encoding gene (CAC1502) were PCR amplified with the Phusion DNA polymerase with total DNA from *C. acetobutylicum* as template and two specific couples of olignonucleotides as primers. With the couples of primers cac-1-cac-2 and cac-3-cac-4, 1493 bp and 999 bp DNA fragments were respectively obtained. Both primers cac-1 and cac-4 introduce a BamHI site while primers cac-2 and cac-3 have complementary 5' extended sequences which introduce a StuI site. DNA fragments cac-1-cac-2 and ac-3-cac-4 were joined in a PCR fusion experiment with primers cac-1 and cac-4 and the resulting fragment was cloned in the pCR4-TOPO-Blunt vector to yield pTOPO:cac15. The cac1502 replacement cassette obtained after BamHI digestion of the resulting plasmid was cloned, at the BamHI, site into pCatUpp to yield the pCatUppΔcac1502 plasmid.

The pCatUppΔcac1502 plasmid was methylated in vivo and used to transform by electroporation *C. acetobutylicum*Δupp. After selection on Petri plates for clones having inserted the pCatUppΔcac1502 plasmid by homologous recombination (resistant to thiamphenicol 20 μg/ml), two colonies were cultured for 24 hours in liquid MS Glucose medium and then subcultured in liquid 2YTG medium without antibiotic. Appropriate dilutions were plated on RCA with 5-FU at 400 μM. To select integrants having excised and lost pCatUppΔcac1502, 5-FU resistant clones were replica plated on both RCA+5FU and RCA with thiamphenicol at 40 μg/ml. To identify clones having lost pCatUppΔcac1502 and possessing a markerless cac1502 deletion, clones resistant to 5-FU and sensitive to thiamphenicol were checked by PCR analysis (with primers cac-0 and cac-5 located outside of the CAC1502 replacement cassette and primers cac-F and cac-R located inside of cac1502). Approximately half of the clones had a cac1502 deletion and half had a wild type genotype for cac1502. The *C. acetobutylicum*ΔuppΔcac1502 was isolated.

Figure 3:
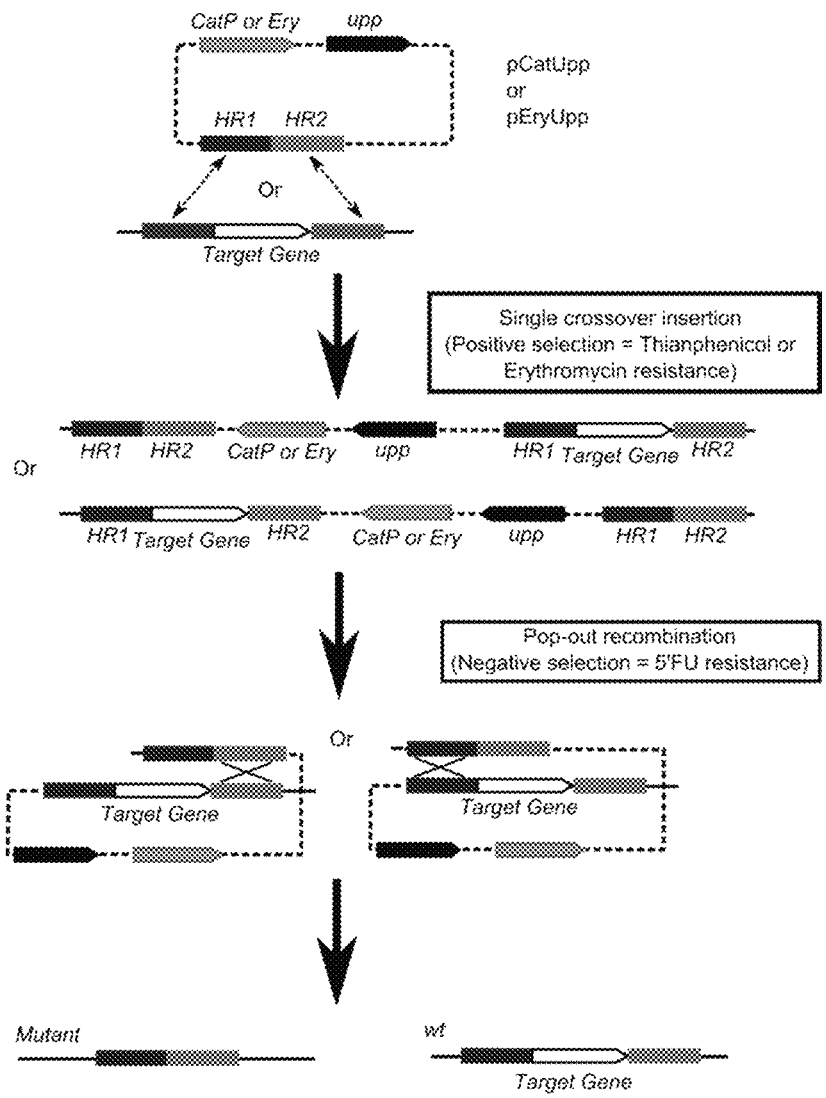
FIG. 3: Schematic representation of the different steps for the deletion of CAC1502.

See FIG. 3 for a schematic representation of succession of steps of the method.

TABLE 2

| Name | SEQ ID No | Primer sequences |
|---|---|---|
| cac-1 | 17 | AAAGGATCCATGCACACTCATAAATTTACTGTAGGAAGTCTG' |
| cac-2 | 18 | GGGGAGGCCTAAAAAGGGGGGTCCCAAATAATATTTGCCATAGTAACCACC |
| cac-3 | 19 | CCCCCTTTTTAGGCCTCCCCTCGAACTTATTAGAATGATATAGATTCCGG |
| cac-4 | 20 | AAAGGATCCTCATTAAATTTCCTCCATTTTAAGCCTGTC |
| cac-0 | 21 | GTGATATAATTTTCCTTTAAATGGAGGAGGATCTG |
| cac-5 | 22 | GCCGTTAATAGACATTATAATTCCATTGGC |
| cac-F | 23 | GAATTCTTAAAAATATTTGGATCATTAAGCGG |
| cac-R | 24 | GTTGTATTGGAATCTTTGTTATTATTTCTCCC |

Example 3: Batch and Continuous Fermentations of Chemicals and Fuels Producing Strains 1—Batch Fermentation of Chemicals and Fuels Producing Strains.

Strains were initially analyzed in anaerobic flask batch cultures in the synthetic medium (MS liquid medium) described by Soni et al (Soni et al, 1987, *Appl. Microbiol. Biotechnol.* 27:1-5) supplemented with 2.5 g/l of ammonium acetate and with glucose, xylose or glycerol as the carbon source. An overnight culture at 35° C. was used to inoculate a 30 ml culture to an OD600 of 0.05. After incubation of the culture for 3 days at 35° C., glucose or glycerol, chemicals and fuel were analyzed by HPLC using a Biorad HPX 97H column for the separation and a refractometer and a UV spectrophotometer for the detection.

2—Continuous Fermentation of Chemicals and Fuels Producing Strains.

The different chemical and fuel producing strains were analyzed in chemostat cultures in the synthetic medium described by Soni et al (Soni et al, 1987) with glucose or glycerol as a carbon source. An overnight culture at 35° C. was used to inoculate a 300 ml fermentors using an anaerobic chemostat protocol.

For this purpose the fermentor was filled with 250 ml of synthetic medium, sparged with nitrogen for 30 min and inoculated with 25 ml of preculture to an optical density (OD600 nm) between 0.05 and 0.1. After 12 hours of batch culture at 35° C., pH 5.5 (regulated using an $NH_4OH$ solution) and an agitation rate of 300 rpm, the fermentor was continuously fed with oxygen free synthetic medium at a dilution rate of 0.05 h-1 while the volume was kept constant by sequential removal of fermented medium. Stability of the culture was followed by products analysis using the HPLC protocol previously described.

Figure 4:
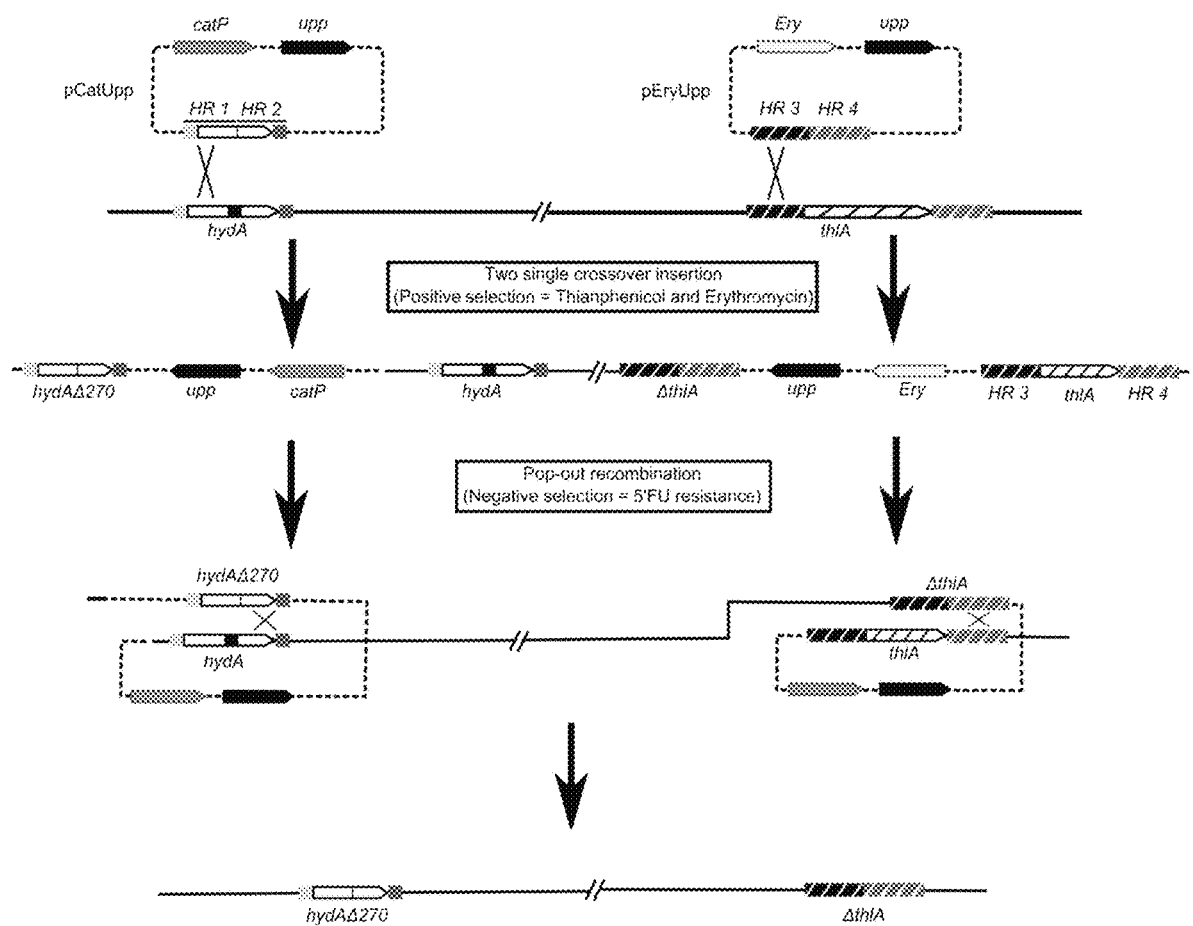
FIG. 4: Schematic representation of the different steps for the simultaneous deletion of hydA and thlA.

Example 4: Construction of a *Clostridium acetobutylicum* Strain Unable to Produce Hydrogen In order to get this strain the thlA and the hydA genes have to be simultaneously inactivated according to the method described in FIG. 4. Integration of the non-replicative plasmid by single crossing over does not inactivate the target genes; The inactivation is only effective after the second crossing over.

1—Construction and Integration by Single Crossing Over of the pEryUppΔthlA Plasmid in the Chromosome of *C. acetobutylicum*ΔuppΔcac1502

Two DNA fragments surrounding the thlA gene (CAC2872) were PCR amplified with the Phusion DNA polymerase with total DNA from *C. acetobutylicum* as template and two specific couples of olignonucleotides as primers. With the couples of primers thl-1-thl-2 and thl-3-thl-4, 1025 bp and 1012 bp DNA fragments were respectively obtained. Both primers thl-1 and thl-4 introduce a BamHI site while primers thl-2 and thl-3 have complementary 5' extended sequences which introduce a StuI site. DNA fragments ΔthlA 1-2 and ΔthlA 3-4 were joined in a PCR fusion experiment with primers thl-1 and thl-4 and the resulting fragment was cloned in the pCR4-TOPO-Blunt vector to yield pTOPO:ΔthlA. The thlA replacement cassette obtained after BamHI digestion of the resulting plasmid was cloned, at the BamHI, site into pEryUpp to yield the pEryUppΔthlA plasmid.

The pEryUppΔthlA plasmid was used to transform by electroporation *C. acetobutylicum*ΔuppΔcac1502. Clones (resistant to erythromycin 20 μg/ml) having inserted the pEryUppΔthlA plasmid by homologous recombination were selected on Petri plates and checked by PCR analysis (with primers thl-0 and thl-5 located outside of the thlA replacement cassette).

The *C. acetobutylicum*ΔuppΔcac1502thlA::pEryUppΔthlA strain was obtained.

| Name | SEQ ID No | Primer sequences |
|---|---|---|
| thl-1 | 25 | AAAAGGATCCAAGCAGTTAATGAAAAGAATATTTTTATTACAGGAAATAC |
| thl-2 | 26 | GTTATTTTTAACAATACTTTAGGCCTTACGGGGTAACAGATAAACCATTTCAATCTA |
| thl-3 | 27 | AATTTAGGAGGTTAGTTAGAAGGCCTAAAGTATTGTTAAAAATAACTCTGTAGAATTATAAATTAG |
| thl-4 | 28 | AAAAGGATCCAAGTTAACAATCATTTCTATTACGCTTTGTTTCC |
| thl-0 | 29 | ACATGGAGATACGACTACAACATTTGCTG |
| thl-5 | 30 | TTCTTTTTATTGCAGTTGCATTTATTAAAAATGC |
| thl-F | 31 | TGGAACATTTCAAGAGAAGAACAAGATGAG |
| thl-R | 32 | GCTCCTCCATTTACATTTACTTTATTCATATC |

2—Construction and Integration by Single Crossing Over of the pCatUppHydA270 Plasmid in the Chromosome of *C. acetobutylicum*ΔuppΔcac1502

A cassette creating an in frame deletion of 270 bp in a region coding for the catalytic domain of the main [Fe—Fe] hydrogenase (HydA) was created using two DNA fragments surrounding this region that were PCR amplified with the Phusion DNA polymerase with total DNA from *C. aceto-* butylicum as template and two specific couples of oligonucleotides as primers. With the couples of primers hyd-1-hyd-2 and hyd-3-hyd-4, 1123 bp and 1008 bp DNA fragments were respectively obtained. Both primers hyd-1 and hyd-4 introduce a BamHI site while primers ldhA-2 and ldhA-3 have complementary. DNA fragments hyd-1-hyd-2 and hyd-3-hyd-4 were joined in a PCR fusion experiment with primers hyd-1 and hyd-4 and the resulting fragment was cloned in the pCR4-TOPO-Blunt vector to yield pTOPO:hydA270. The hydA replacement cassette obtained after BamHI digestion of the resulting plasmid was cloned, at the BamHI, site into pCatUpp to yield the pCatUppΔhydA270 plasmid The pCatUppΔhyda270 plasmid was used to transform by electroporation C. acetobutylicumΔuppΔcac1502thlA:: pEryUppΔthlA. Clones (resistant to erythromycin 20 µg/ml and thiamphenicol 20 µg/ml) having inserted the pCatUppΔhyda270 plasmid by homologous recombination were selected on Petri plates and checked by PCR analysis (with primers hyd-0 and hyd-5 located outside of the hydA replacement cassette). The C. acetobutylicumΔuppΔcac1502thlA::pEryUppΔthlΔhydA:: pCatUppΔhyda270 strain was obtained.

| Name | SEQ ID No | Primer sequences |
|---|---|---|
| Hyd-1 | 33 | AAAGGATCCGTTTTTCTTAATATTTACCATATTGCACCTCCC |
| Hyd-2 | 34 | ATATCTCTTAAGCTGTTAGTTTCCATTATAGTCATATCTGCACCAAAG |
| Hyd-3 | 35 | CAGATATGACTATAATGGAAACTAACAGCTTAAGAGATATTGATGCATCC |
| Hyd-4 | 36 | AAAGGATCCCTGGTACATCAGTATACGAAACAATGCC |
| Hyd-0 | 37 | CATGTTCTATTGTTACTATGGAAGAGGTAGTAG |
| Hyd-5 | 38 | GCAGTTATTATAAATGCTGCTACTAGAGC |
| Hyd-F | 39 | GAAGCTACTGAACTTTTAGGCAGAG |
| Hyd-R | 40 | CTGCTTCATATTTTTATCATTACAAGGC |

3—Simultaneous Inactivation of thlA and hydA in C. acetobutylicumΔuppΔcac1502

To simultaneously inactivate thlA and hydA, two colonies of the C. acetobutylicumΔuppΔcac1502thlA:: pEryUppΔthlΔhydA:: pCatUppΔhyda270 strain were cultured for 24 hours in liquid MS Glucose medium and then subcultured in liquid 2YTG medium without antibiotic. Appropriate dilutions were plated on RCA with 5-FU at 400 µM. To select integrants having excised and lost both the pEryUppΔthlA and the pCatUppΔhyda270 plasmids, 5-FU resistant clones were replica plated on both RCA+5FU, RCA with erythromycin 40 µg/ml and RCA with thiamphenicol at 40 µg/ml. Clones resistant to 5-FU and sensitive to erythromycin and thiamphenicol were checked by PCR analysis (with primers thla-0 and thla-5 located outside of the thlA replacement cassette and primers thl-D and thl-R located inside of thlA and with primers hyd-0 and hyd-5 located outside of the hydA replacement cassette and primers hyd-D and hyd-R located inside of hydA). All the clones resistant to 5-FU and sensitive to erythromycin and thiamphenicol possess inactivated thlA and hydA genes. The C. acetobutylicumΔuppΔcac1502 ΔthlAΔhydA270 strain was obtained.

The strain was evaluated in MS glucose batch culture as described in example 2. Ethanol and lactate were the two major products with small amount of acetate and glycerol.

Table 2 shows the ethanol and lactate yield on glucose of the C. acetobutylicumΔuppΔcac1502 ΔthlAΔhydA270 strain.

| Strain | Ethanol yield (g/g) | Lactate yield (g/g) |
|---|---|---|
| C. acetobutylicumΔuppΔcac1502 ΔthlAΔhydA270 | 0.4 | 0.1 |

Example 5: Construction of a Clostridium acetobutylicum Strain Unable to Produce Hydrogen and Producing L-Lactate at High Yield The C. acetobutylicumΔuppΔcac1502 ΔthlAΔhydA270 strain produced ethanol and lactate. In order to obtain a strain that produce L-lactate at high yield, the pSOL1 megaplasmid was cured from the C. acetobutylicumΔuppΔcac1502 ΔthlAΔhydA270 strain by serial subcultures (20) in MS glucose medium. Cells having lost the pSOL1 megaplasmid were identified on an RCA agar plate containing starch (2%) and glucose (0.2%) and after iodine staining as they do not produce halo of starch hydrolysis (Sabathe et al, 2002). Approximately 1 colony out of 1000 has lost the pSOL1 megaplasmid after 20 subcultures. The C. acetobutylicumΔuppΔcac1502 ΔthlAΔhydA270 ΔpSOL strain was obtained.

Figure 5:
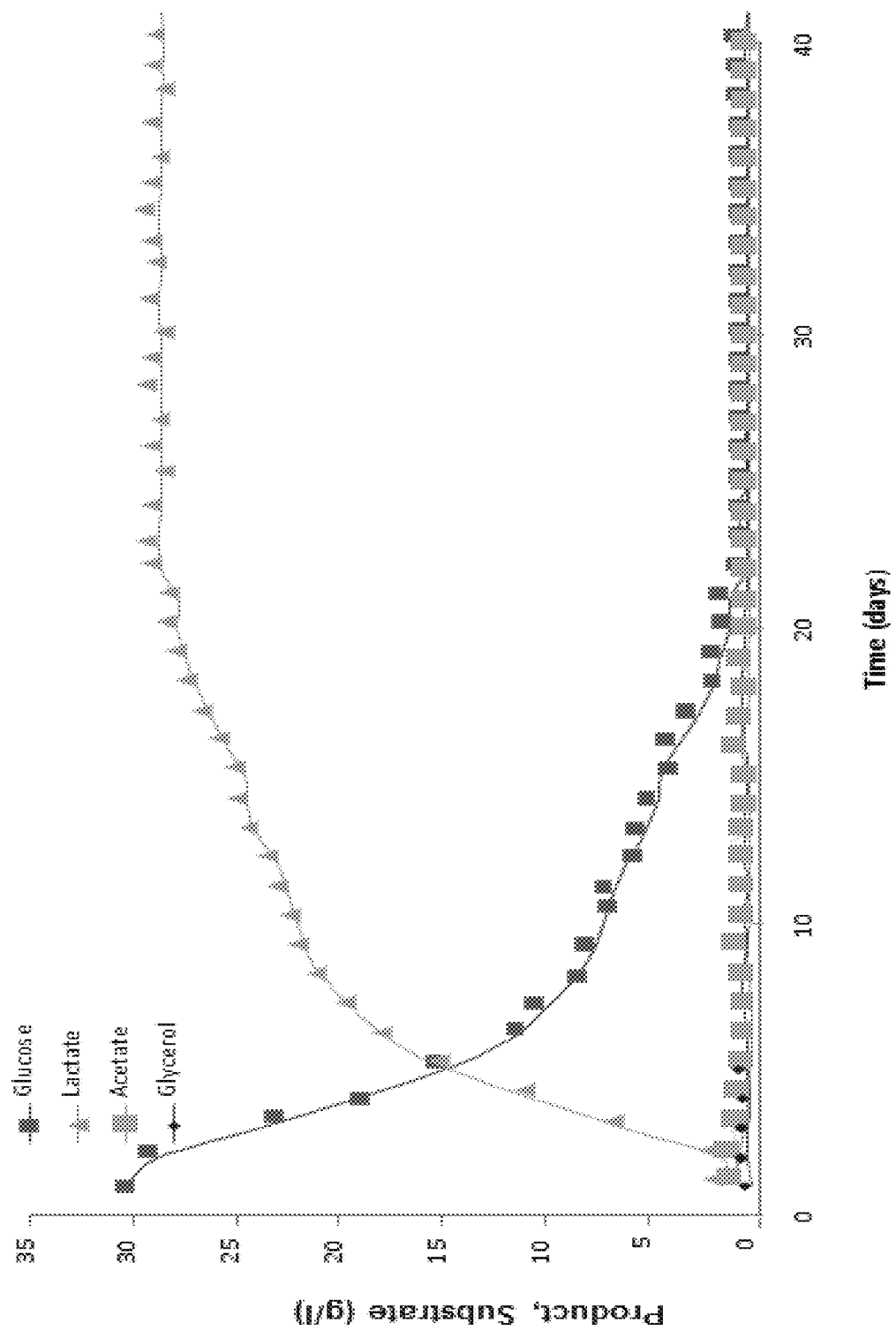
FIG. 5: Continuous production of lactate by the C. acetobutylicum ΔuppΔcac1502 ΔthlAΔhydA270ΔpSOL. Experimental conditions: MS glucose medium 30 g/l, pH 6.5, Temp 35° C., D=0.05 h-1.

This strain was used for the continuous production of lactate in MS glucose medium. The results are shown in FIG. 5. The best yield on glucose titer and productivities obtained were respectively 0.95 g/g, 28.6 g/l and 1.37 g/l·h Example 6: Construction of a Clostridium acetobutylicum Strain Unable to Produce Hydrogen and Producing Ethanol at High Yield The C. acetobutylicumΔuppΔcac1502 ΔthlAΔhydA270 strain produced ethanol and lactate. In order to obtain a strain that produce ethanol at high yield, the ldhA gene (CAC0267) encoding the main L-lactate dehydrogenase was inactivated in the C. acetobutylicumΔuppΔcac1502 ΔthlAΔhydA270 strain.

1—Deletion of the ldhA Gene Encoding the Main L-Lactate Dehydrogenase in Clostridium acetobutylicum Two DNA fragments surrounding the LdhA coding sequence (CAC0267) were PCR amplified with the Phusion DNA polymerase with total DNA from C. acetobutylicum as template and two specific couples of olignonucleotides as primers. With the couples of primers ldh-1-ldh-2 and ldh-3-ldh-4, 1135 bp and 1177 bp DNA fragments were respectively obtained. Both primers ldh-1 and ldh-4 introduce a BamHI site while primers ldh-2 and ldh-3 have complementary 5' extended sequences which introduce a StuI site. DNA fragments ldh-1-ldh-2 and ldh-3-ldh-4 were joined in a PCR fusion experiment with primers ldh-1 and ldh-4 and the resulting fragment was cloned in the pCR4-TOPO-Blunt vector to yield pTOPO:ldhA. The ldhA replacement cassette obtained after BamHI digestion of the resulting plasmid was cloned, at the BamHI, site into pCatUpp to yield the pCatUppΔldhA plasmid. The pCatUppΔldhA plasmid was used to transform by electroporation C. acetobutylicumΔuppΔcac1502 ΔthlAΔhydA270. After selection on Petri plates for clones having inserted the pCatUppΔldhA plasmid by homologous recombination (resistant to thiamphenicol 20 μg/ml), two colonies were cultured for 24 hours in liquid MS Glucose medium and then subcultured in liquid 2YTG medium without antibiotic. Appropriate dilutions were plated on RCA with 5-FU at 400 μM. To select integrants having excised and lost pCatUppΔldhA, 5-FU resistant clones were replica plated on both RCA+5FU and RCA with thiamphenicol at 40 μg/ml. To identify clones having lost pCatUppΔldhA and possessing a markerless ldhA deletion, clones resistant to 5-FU and sensitive to thiamphenicol were checked by PCR analysis (with primers ldh-0 and ldh-5 located outside of the ldhA replacement cassette and primers ldh-D and ldh-R located inside of ldhA). Approximately half of the clones had a ldhA deletion and half had a wild type genotype for ldhA. The *C. acetobutylicum*ΔuppΔcac1502 ΔthlAΔhydA270 ΔldhA was isolated.

Example 8: Construction of a *Clostridium acetobutylicum* Strain Unable to Produce Hydrogen and Producing n-Butanol at High Yield The *C. acetobutylicum*ΔuppΔcac1502 ΔthlAΔhydA270 ΔldhA strain produced ethanol at high yield. In order to obtain a strain that produce n-butanol at high yield, the ptb and buk genes encoding the last two enzymatic steps of the butyrate pathway were first deleted. Then to restore n-butanol production and to obtain a high n-butanol to ethanol ratio a synthetic atoB gene coding for the thiolase of *Escherichia coli* was introduced at the ΔthlA locus of the *C. acetobutylicum*ΔuppΔcac1502 ΔthlAΔhydA270 ΔldhA strain.

1—Deletion of the Ptb and Buk Genes Encoding the Last Two Steps of the Butyrate Pathway in *Clostridium acetobutylicum*

| Name | SEQ ID N° | Primer sequences |
|------|-----------|------------------|
| ldh-1 | 41 | AAAAGGATCCGCTTTAAAATTTGGAAAGAGGAAGTTGTG |
| ldh-2 | 42 | GGGGAGGCCTAAAAAGGGGGTTAGAAATCTTTAAAAATTTCTCTATAGAGCCCATC |
| ldh-3 | 43 | CCCCCTTTTTAGGCCTCCCCGGTAAAAGACCTAAACTCCAAGGGTGGAGGCTAGGTC |
| ldh-4 | 44 | AAAAGGATCCCCCATTGTGGAGAATATTCCAAAGAAGAAAATAATTGC |
| ldh-0 | 45 | CAGAAGGCAAGAATGTATTAAGCGGAAATGC |
| ldh-5 | 46 | CTTCCCATTATAGCTCTTATTCACATTAAGC |
| ldh-F | 47 | GGATTTGTTGGTTCTTCTACAGTATTTGCG |
| ldh-R | 48 | CCTCTATAATATCCTTCACTCCGTTAATTCC |

Figure 6:
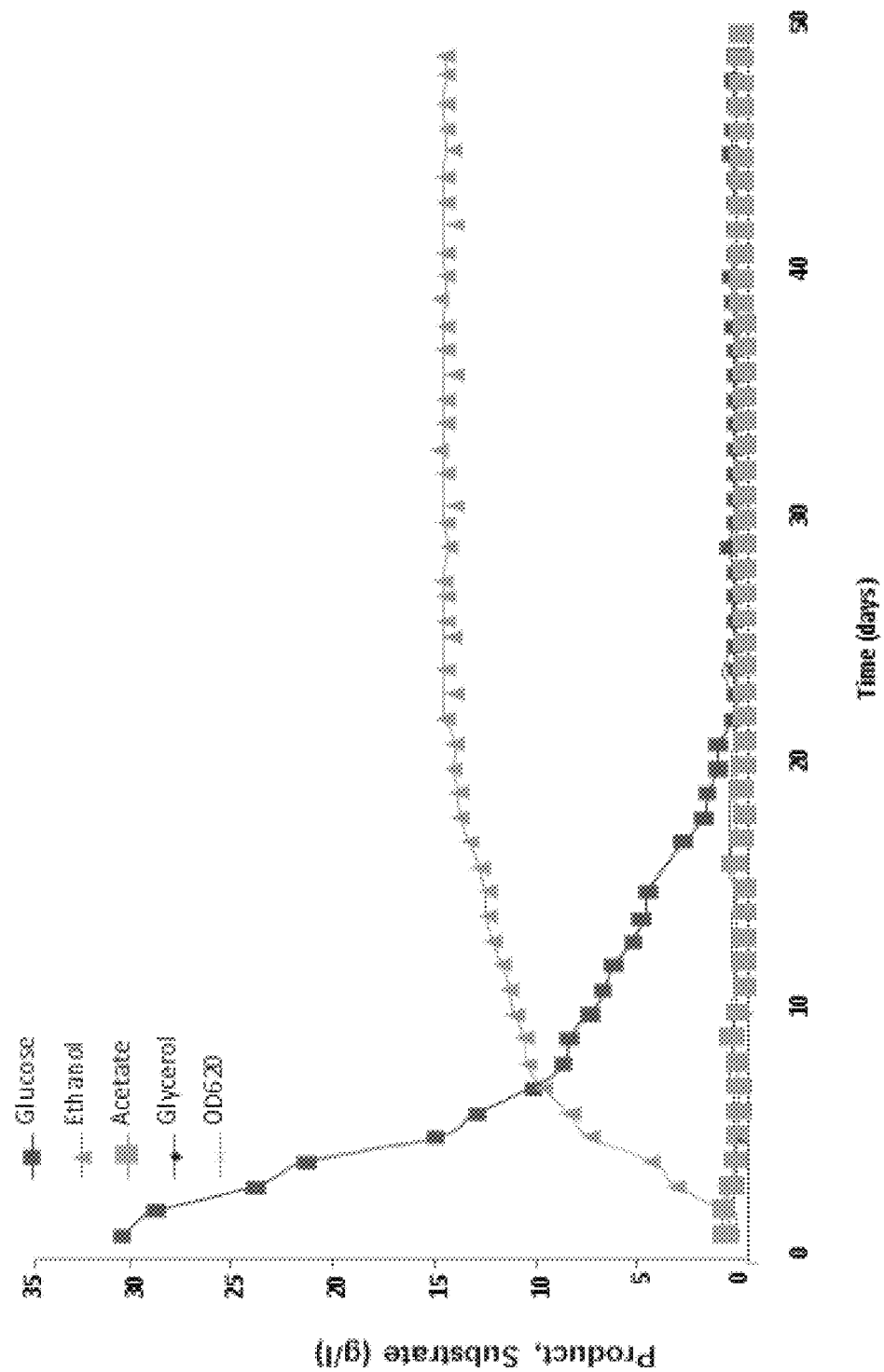
FIG. 6: Continuous production of ethanol by the C. acetobutylicum ΔuppΔcac1502 ΔthlAΔhydA270ΔldhA. Experimental conditions: MS glucose medium 30 g/l, pH 5.2, Temp 35° C., D=0.05 h-1

2—Production of Ethanol in Continuous Culture of *C. acetobutylicum*ΔuppΔcac1502 ΔthlAΔhydA270 ΔldhA This strain was used for the continuous production of ethanol in MS glucose medium. The results are shown in FIG. 6. The best yield on glucose titer and productivities obtained were respectively 0.45 g/g, 13.5 gl and 0.78 g/l·h

Figure 7:
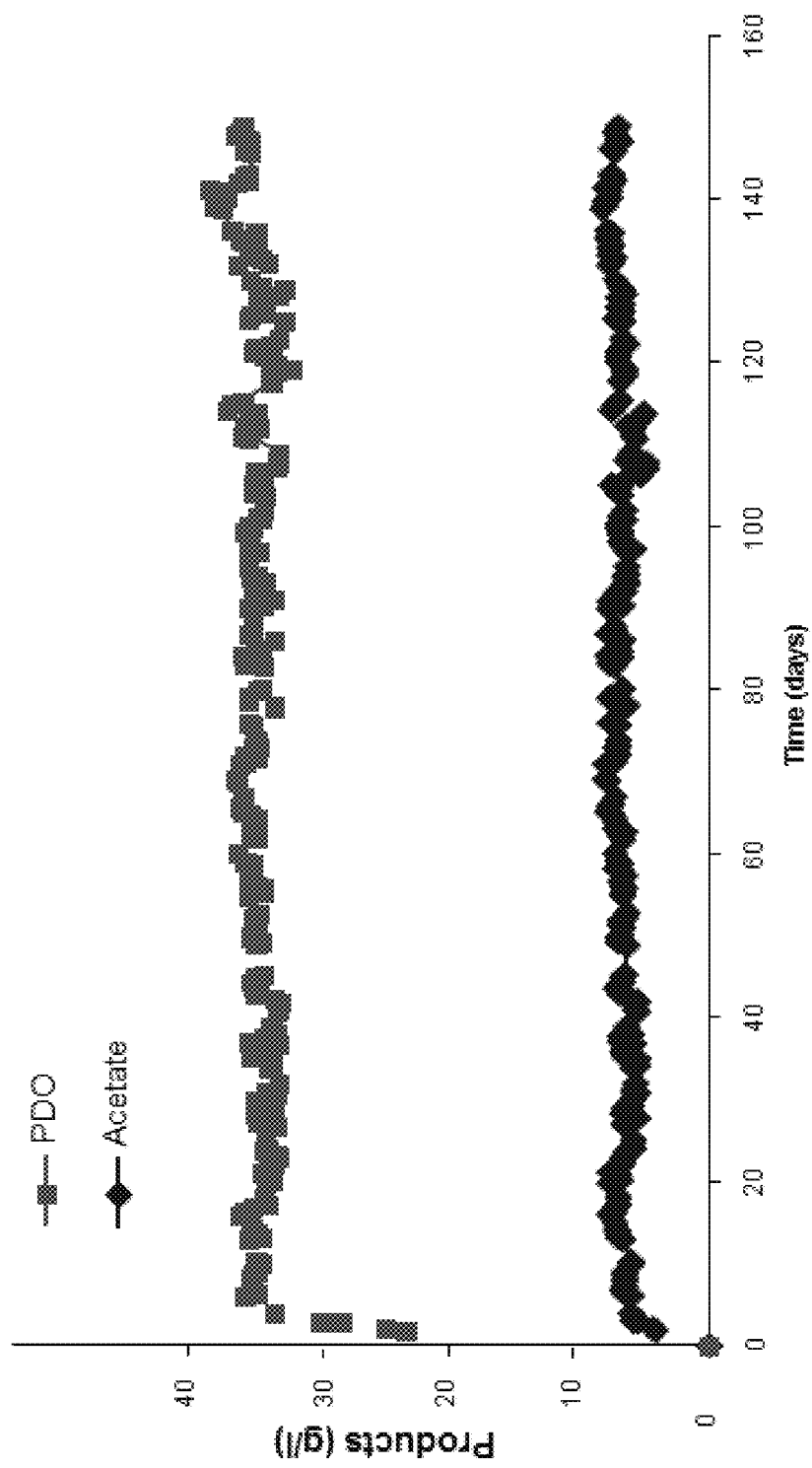
FIG. 7: Continuous production of 1, 3 propanediol by the C. acetobutylicum ΔuppΔcac1502 ΔthlAΔhydA270 ΔpSOL (pSPD5). Experimental conditions: MS glycerol medium 60 g/l, pH 6.3, Temp 35° C., D=0.05 h-1

Example 7: Construction of a *Clostridium acetobutylicum* Strain Unable to Produce Hydrogen and Producing 1, 3 Propanediol at High Yield The *C. acetobutylicum*ΔuppΔcac1502 ΔthlAΔhydA270 ΔpSOL strain produced lactate at high yield. In order to obtain a strain that converts glycerol to 1, 3 propanediol at high yield, the pSPD5 plasmid (Raynaud et al) that carries the genes coding for the B12-independent 1, 3 propanediol pathway from *Clostridium butyricum* was used to transform by electroporation the *C. acetobutylicum*ΔuppΔcac1502 ΔthlAΔhydA270 ΔpSOL strain. After selection on Petri plates for clones having containing the replicative pSPD5 plasmid (resistant to erythromycin at 40 μg/ml), 10 colonies were cultured for 24 hours in liquid 2YTGlycerol medium and then subcultured in liquid MS Glycerol medium. The clone having the fastest growth in MS glycerol medium was designated *C. acetobutylicum*ΔuppΔcac1502 ΔthlAΔhydA270 ΔpSOL (pSPD5). This strain was used for the continuous production of 1, 3 propanedio in MS glycerol medium. The results are shown in FIG. 7. The best yield on glycerol, titer and productivities obtained were respectively 0.6 g/g, 36 g/l and 1.8 g/l·h Two DNA fragments surrounding the Ptb+Buk coding sequence (CAC0267) were PCR amplified with the Phusion DNA polymerase with total DNA from *C. acetobutylicum* as template and two specific couples of olignonucleotides as primers. With the couples of primers ptuk-1-ptuk-2 and ptuk-3-ptuk-4, 1255 bp and 969 bp DNA fragments were respectively obtained. Both primers ptuk-1 and ptuk-4 introduce a BamHI site while primers ptuk-2 and ptuk-3 have complementary 5' extended sequences which introduce a NruI site. DNA fragments ptuk-1-ptuk-2 and ptuk-3-ptuk-4 were joined in a PCR fusion experiment with primers ptuk-1 and ptuk-4 and the resulting fragment was cloned in the pCR4-TOPO-Blunt vector to yield pTOPO:ptbbuk. The ptb-buk replacement cassette obtained after BamHI digestion of the resulting plasmid was cloned, at the BamHI, site into pCatUpp to yield the pCatUppΔptbbuk plasmid.

The pCatUppΔptbbuk plasmid was used to transform by electroporation *C. acetobutylicum*ΔuppΔcac1502 ΔthlAΔhydA270 ΔldhA. After selection on Petri plates for clones having inserted the pCatUppΔptbbuk plasmid by homologous recombination (resistant to thiramphenicol 20 μg/ml), two colonies were cultured for 24 hours in liquid MS Glucose medium and then subcultured in liquid 2YTG medium without antibiotic. Appropriate dilutions were plated on RCA with 5-FU at 400 μM. To select integrants having excised and lost pCatUppΔptbbuk, 5-FU resistant clones were replica plated on both RCA+5FU and RCA with thiamphenicol at 40 μg/ml. To identify clones having lost pCatUppΔptbbuk and possessing a markerless ptb-buk deletion, clones resistant to 5-FU and sensitive to thiamphenicol were checked by PCR analysis (with primers ptuk-0 and ptuk-5 located outside of the ptb-buk replacement cassette and primers ptuk-D and ptuk-R located inside of ptb). Approximately half of the clones had a ptb-buk deletion and half had a wild type genotype for ptb-buk. The *C. acetobutylicum*ΔuppΔcac1502 ΔthlAΔhydA270 ΔldhA Δptb-buk was isolated.

| Name | SEQ ID No | Primer sequences |
|---|---|---|
| ptuk-1 | 49 | CTAGAATTAAGGATCCTAGATGCACGTATG |
| ptuk-2 | 50 | CTTCTGCAAGTGCAAGAAGTTCGCGACACTGGTCGTACACTCCCTTTTACTATTTAATTATC |
| ptuk-3 | 51 | AAGGGAGTGTACGACCAGTGTCGCGAACTTCTTGCACTTGCAGAAGGTGGAC |
| ptuk-4 | 52 | AAAAGGATCCTCTAAATTCTGCAATATATGCCCCCCC |
| ptuk-0 | 53 | ATAACAGGATATATGCTCTCTGACGCGG |
| ptuk-5 | 54 | GATCATCACTCATTTTAAACATGGGGCC |
| ptuk-F | 55 | CTTTAAATGCTGTAGTTGGAAGAGGCGG |
| ptuk-R | 56 | TAAGTAACTAACAACTCCGCCTTTGCCG |

2—Insertion of a Synthetic atoB Gene at the ΔthlA Locus of *C. acetobutylicum*ΔuppΔcac1502 ΔthlAΔhydA270 ΔldhAΔptb-buk to Restore n-Butanol Production A synthetic atoB operon coding for the AtoB thiolase of *E. coli* was synthesize as follow. A synthetic atoB gene was designed with both an optimized synthetic RBS (translation initiation rate was calculated to be 60217, a value similar to the translation initiation rate of thlA) and an harmonized codon usage for *C. acetobutylicum*. The synthetic gene was synthesized by Life technology (atoBs) with a BamHI site in 5' and an SfoI site in 3' and was cloned in a BamHI-SfoI digested pSOS95 to yield pSOS95atoBs.

The synthetic atoB gene was PCR amplified with the Phusion DNA polymerase with pSOSatoBs as template and the Atob-1 and Atob-2 olignonucleotides as primers. This DNA fragment was directly cloned into the StuI linearized pEryUppΔthlA by homologous recombination using the GeneArt® Seamless Cloning & Assembly kit to yield the pEryUppAtoB plasmid.

The pEryUppAtoB plasmid was used to transform by electroporation *C. acetobutylicum*ΔuppΔcac1502 ΔthlAΔhydA270 ΔldhA Δptb-buk. After selection on Petri plates for clones having inserted the pEryUppAtoB plasmid by homologous recombination (resistant to erythromycin 20 μg/ml), two colonies were cultured for 24 hours in liquid MS Glucose medium and then subcultured in liquid 2YTG medium without antibiotic. Appropriate dilutions were plated on RCA with 5-FU at 400 μM. To select integrants having excised and lost pEryUppAtoB, 5-FU resistant clones were replica plated on both RCA+5FU and RCA with erythromycin at 40 μg/ml. To identify clones having lost pEryUppAtoB and possessing an atoB insertion, (clones

| Name | SEQ ID No | Primer sequences |
|---|---|---|
| atob-1 | 57 | ACTTATGAAATAGATTGAAATGGTTTATCTGTTACCCCGTAGGATCCTCGAAGGTCGACCACCCAG |
| atob-2 | 58 | CTAATTTATAATTCTACAGAGTTATTTTTAACAATACTTTTTAGTTTAGTCGTTCTATTACCATAGCTATCCCTT |
| Synthetic atoB | 59 | AGGATCCTCGAAGGTCGACCACCCAGAATAAAGGAGCCATTAATGAAAAACTGCGTGATTGTGAGCGCTGTGCGTACGGCCATTGGTAGCTTTAATGGTAGCCTAGCCAGCACAAGTGCTATTGACTTAGGGGCTACGGTGATAAAAGCTGCTATAGAACGTGCCAAAATTGATAGCCAGCACGTGGATGAAGTAATAATGGGTAATGTATTGCAGGCTGGGTTAGGGCAGAACCCAGCTCGTCAAGCCTTATTGAAAAGTGGGTTAGCCGAAACGGTATGTGGGTTCACGGTGAACAAAGTGTGCGGTAGCGGTCTAAAAAGCGTAGCTCTAGCTGCTCAAGCTATACAAGCCGGTCAAGCTCAAAGTATAGTAGCTGGGGGTATGGAAAACATGAGCTTGGCTCCGTACTTGCTAGATGCCAAAGCCAGAAGCGGTTATCGTCTAGGGGACGGGCAAGTGTATGACGTGATTTTAAGAGATGGATTAATGTGTGCTACACATGGTTATCATATGGGGATAACAGCTGAAAATGTAGCCAAAGAGTACGGGATAACACGTGAAATGCAAGATGAATTAGCTCTGCATAGCCAACGTAAAGCTGCCGCTGCCATAGAGAGCGGTGCCTTTACGGCTGAAATTGTGCCAGTGAACGTGGTGACGCGAAAGAAAACATTCGTGTTCAGCCAGGACGAATTCCCAAAAGCTAACAGCACGGCCGAAGCTTTGGGTGCCCTAAGACCAGCTTTTCGATAAAGCCGGGACGGTGACAGCCGGGAATGCTAGCGGTATAAATGACGGTGCCGCTGCCTTAGTAATAATGGAAGAAAGCGCTGCTTTAGCCGCCGGACTAACACCGTTAGCAGAATAAAAAGCTATGCTAGTGGTGGAGTACCGCCGGCCCTAATGGGTATGGGGCCGGTGCCGGCTACGCAGAAAGCTTTGCAGTTAGCTGGGTTACAGTTAGCTGATATAGATCTAATAGAGGCCAACGAAGCCTTTGCCGCCCAATTCCTAGCTGTGGGGAAAAATTTAGGATTTGATAGCGAGAAAGTAAACGTGAATGGAGGGGCTATTGCTCTAGGGCATCCGATTGGTGCTAGCGGTGCCCGTATATTAGTGACGCTGTTGCATGCTATGCAAGCCAGAGATAAAACGTTAGGGTTAGCCACGTTATGTATAGGAGGAGGTCAAGGGATAGCTATGGTAATAGAACGACTAAACTAAGGCGCCA | resistant to 5-FU and sensitive to erythromycin) were checked by PCR analysis (with primers Thla-0 and Thla-5 located outside of the ΔthlA locus). Less than 10% of the clones had an atoB insertion all the other clones having a ΔthlA genotype. The C. acetobutylicumΔuppΔcac1502 ΔthlA::atoBΔhydA270 ΔldhA Δptb-buk was isolated.

Figure 8:
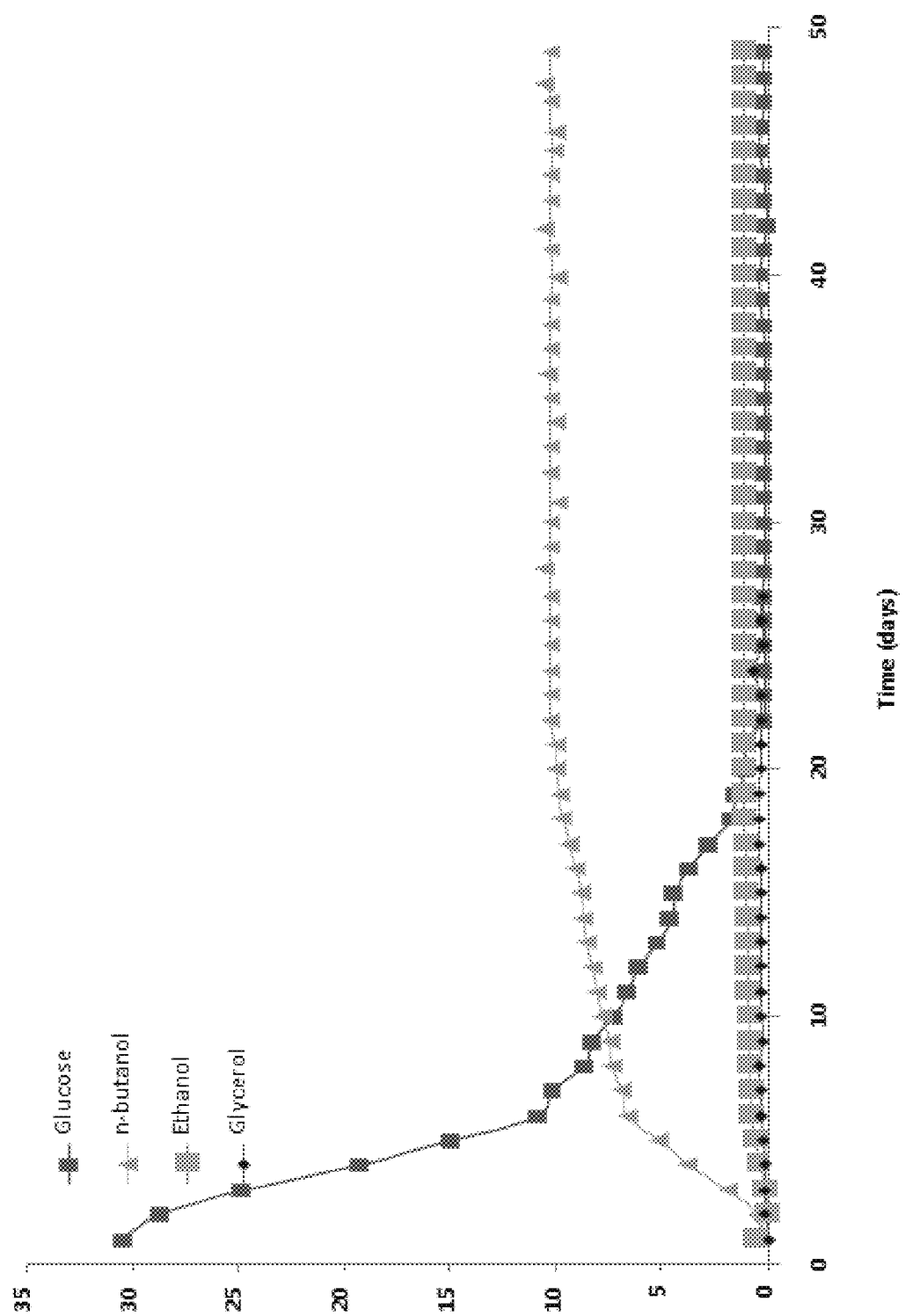
FIG. 8: Continuous production of n-butanol by the C. acetobutylicum ΔuppΔcac1502 ΔthlA::atoBΔhydA270 ΔldhA Δptb-buk. Experimental conditions: MS glucose medium 30 g/l, pH 5.2, Temp 35° C., D=0.05 h-1

3—Production of n-Butanol in Continuous Culture of C. acetobutylicumΔuppΔcac1502 ΔthlA::atoBΔhydA270 ΔldhA Δptb-buk This strain was used for the continuous production of n-butanol in MS glucose medium as described in example 2. The results are shown in FIG. 8. The best n-butanol yield on glucose, titer and productivities obtained were respectively 0.34 g/g, 10.3 gl and 0.52 g/l·h

Example 9: Construction of a *Clostridium acetobutylicum* Strain Unable to Produce Hydrogen and Producing Isobutanol at High Yield The C. acetobutylicumΔuppΔcac1502 ΔthlAΔhydA270 ΔpSOL strain produced lactate at high yield. In order to obtain a strain that produces isobutanol at high yield, we first created an "homologous isobutanol pathway" by overexpressing from a plasmid (pISOB) the alsS (CAC3652), ilvC (CAC0091), ilvD (CAC3170) and pdc (CAP0025) genes. Then, to improve the isobutanol yield the ldhA gene was deleted using the pCatUppΔldhA plasmid.

1—Construction of a *Clostridium acetobutylicum* Strain for "Homologous Isobutanol Production".

The pISOB vector was constructed in two steps:

1.1 Construction of the ilvC-ilvD-pdc Operon

The ilvC gene was PCR amplified with the Phusion DNA polymerase using C. acetobutylicum ATCC824 genomic DNA as template and primers ilvC-F and ilvC-R. After digestion by BamHI and SfoI, this PCR product was cloned into the pSOS94 plasmid previously digested by the same enzymes, giving the pSOS94::ilvC plasmid The ilvD gene was PCR amplified with the Phusion DNA polymerase using C. acetobutylicum ATCC824 genomic DNA as template and primers ilvD-F and ilvD-R. After digestion by XhoI and SfoI, this PCR product was cloned into the pSOS94::ilvC plasmid previously digested by the same enzymes, giving the pSOS94::ilvC-ilvD plasmid The pdc gene was PCR amplified with the Phusion DNA polymerase using C. acetobutylicum ATCC824 genomic DNA as template and primers pdc-F and pdc-R. After digestion by AvrII and SfoI, this PCR product was cloned into the pSOS94::ilvC-ilvD plasmid previously digested by the same enzymes, giving the pSOS94::ilvC-ilvD-pdc plasmid The ilvC-ilvD-pdc operon containing the ptb promoter and the adc transcriptional was PCR amplified with the Phusion DNA polymerase using the pSOS94::ilvC-ilvD-pdc plasmid as template and the primers ilvCD-pdc-F and ilvCD-pdc-R. After digestion by SalI, the Pptb-ilvC-ilvD-pdc-adcTT operon was cloned into the pSOS95 plasmid previously digested by the same enzyme, giving the pSOS95::ilvC-ilvD-pdc plasmid.

1.2 Construction and Insertion of the als Monocistronic Operon

The als gene and its own transcriptional terminator was PCR amplified with the Phusion DNA polymerase using C. acetobutylicum ATCC824 genomic DNA as template and primers Als-F and Als-R.

After digestion by NotI and SacII, this PCR product was cloned into the pSOS95::ilvC-ilvD-pdc plasmid previously digested by the same enzymes, giving the pSOS95::als-ilvC-ilvD-pdc plasmid The thlA promoter (pthlA) was PCR amplified with the Phusion DNA polymerase using C. acetobutylicum ATCC824 genomic DNA as template and primers pthlA-F and pthlA-R After digestion by NotI and NcoI, this PCR product was cloned into the pSOS95::als-ilvC-ilvD-pdc plasmid previously digested by the same enzymes, giving the final pISOB plasmid. The unique NotI and NcoI sites in the final plasmid allow the easy replacement of the WT pthlA promoter by others of different strengths and subsequent variation of the expression level of the als gene.

pISOB. plasmid was used to transform by electroporation the C. acetobutylicum ΔuppΔcac1502 ΔthlAΔhydA270 ΔpSOL strain. After selection on Petri plates for clones resistant to erythromycin at 40 µg/ml, C. acetobutylicumΔuppΔcac1502 ΔthlAΔhydA270 ΔpSOL (pISOB) was obtained.

| Name | SEQ ID No | Primer sequence |
|---|---|---|
| ilvC-F | 60 | AAAAGGATCCTATTTTTTAGGAGGAAAAGTGTTATGGAAG |
| ilvC-R | 61 | AAAAGGCGCCAAAAAACTCGAGGCCCCCTATATTATTTACTATTCGTTTG |
| ilvD-F | 62 | AAAACTCGAGAAGGAGTGATTTATGTGAATTCTGATAAGG |
| ilvD-R | 63 | AAAAGGCGCCAAAAAACCTAGGTCATCACTCCTTTGTACTATGAAAAACTGC |
| pdc-F | 64 | AAAACCTAGGTGGAGGTGACAATTTTGAAGAGTG |
| pdc-R | 65 | AAAAGGCGCCTATTTAAAATGCTATATTTTGAACTAATTATTTTGATTTGC |
| ilvCD-pdc-F | 66 | AAAGTCGACAAGCGGCCGCAAAAACCGCGGTGTGGATGGAGTTAAGTCAGCAGAAAG |
| ilvCD-pdc-R | 67 | CCATGATTACGAATTCTATGAGTCGACATTA |
| als-F | 68 | AAAGCGGCCGCAAAAAACCATGGTTAAAAAAATAATTTAGAGTGAGAATAAGGGG |
| als-R | 69 | AAACCGCGGCAGAATTAAAAGCTAAATAAAATAGAGTGCTG |

-continued

| Name | SEQ ID No | Primer sequence |
|---|---|---|
| pthlA-F | 70 | AAAGCGGCCGCTTTTTAACAAAATATATTGATAAAAATAATAATAGTGGG |
| pthlA-R | 71 | AAACCATGGTACGGGGTAACAGATAAACCATTTC |

2—Improvement of the Isobutanol Yield by Inactivation of ldhA in C. acetobutylicumΔuppΔcac1502 ΔthlAΔhydA270 ΔpSOL (pISOB)

The pCatUppΔldhA plasmid was used to transform by electroporation C. acetobutylicumΔuppΔcac1502 ΔthlAΔhydA270 ΔpSOL (pISOB). After selection on Petri plates for clones having inserted the pCatUppΔcac1502 plasmid by homologous recombination (resistant to chloramphenicol 20 μg/ml), two colonies were cultured for 24 hours in liquid MS Glucose medium and then subcultured in liquid 2YTG medium without antibiotic. Appropriate dilutions were plated on RCA with 5-FU at 400 μM. To select integrants having excised and lost pCatUppΔldhA, 5-FU resistant clones were replica plated on both RCA+5FU and RCA with thiamphenicol at 40 μg/ml. To identify clones having lost pCatUppΔldhA and possessing a markerless ldhA deletion, clones resistant to 5-FU and sensitive to thiamphenicol were checked by PCR analysis (with primers ldhA-0 and ldhA-5 located outside of the ldhA replacement cassette and primers ldhA-D and ldhA-R located inside of ldhA). Less than 10% of the clones had an ldhA deletion all the other clones having a wild type genotype for ldhA. The C. acetobutylicumΔuppΔcac1502 ΔthlAΔhydA270 ΔpSOL ΔldhA (pISOB) strain was isolated.

The strain was evaluated in MS glucose batch culture as described in example 2. Isobutanol was the major product with small amount of acetate and glycerol.

Example 10: Construction of a Clostridium acetobutylicum Strain Unable to Produce Hydrogen and Producing Acetate at High Yield The C. acetobutylicumΔuppΔcac1502 ΔthlAΔhydA270 ΔpSOL strain produced lactate at high yield. In order to obtain a strain that produces acetate at high yield, we first created an "homologous non oxidative glycolytic pathway" by overexpressing from a plasmid the xfp (CAC1343), glpX (CAC1088), rpiB (CAC2880) and rpe (CAC1730) genes and from the chromosome the tal-tkt (CAC1347-1348) operon. Then, to improve the acetate yield the gapC gene was inactivated.

1—Construction of a Clostridium acetobutylicum Strain Expressing an "Homologous Non Oxidative Glycolytic Pathway".

The pCatUppPthlTakt plasmid was constructed to replace the natural promoter of the tal (CAC1347)-tkt (CAC1348)-operon by the thiolase promoter. Two DNA fragments surrounding the natural promoter region of the tal (CAC1347)-tkt (CAC1348)-operon were PCR amplified with the Phusion DNA polymerase with total DNA from C. acetobutylicum as template and two specific couples of olignonucleotides as primers. With the couples of primers takt-1-takt-2 and takt-3-takt-4, 1096 bp and 1078 bp DNA fragments were respectively obtained. Both primers takt-1 and takt-4 introduce a BamHI site while primers takt-2 and takt-3 have complementary 5' extended sequences which introduce a StuI site. DNA fragments takt-1-takt-2 and takt-3-takt-4 were joined in a PCR fusion experiment with primers takt-1 and takt-4 and the resulting fragment was cloned in the pCR4-TOPO-Blunt vector to yield pTOPO:takt. The takt replacement cassette obtained after BamHI digestion of the resulting plasmid was cloned, at the BamHI, site into pEryUpp to yield the pCatpUppTakt plasmid. The pthl promotor was PCR amplified with the Phusion DNA polymerase with pSOS95 as template and the pthl-1 and pthl-2 olignonucleotides as primers. This DNA fragment was directly cloned into the StuI linearized pCatpUppTakt by homologous recombination using the GeneArt® Seamless Cloning & Assembly kit to yield the pCatpUppPthlTakt plasmid. The pCatpUppPthlTakt plasmid was used to transform by electroporation C. acetobutylicum. After selection on Petri plates for clones having inserted the pCatpUppPthlTakt plasmid by homologous recombination (resistant to Thiamphenicol 20 μg/ml), two colonies were cultured for 24 hours in liquid MS Glucose medium and then subcultured in liquid 2YTG medium without antibiotic. Appropriate dilutions were plated on RCA with 5-FU at 400 μM. To select integrants having excised and lost pCatpUppPthlTakt, 5-FU resistant clones were replica plated on both RCA+5FU and RCA with thiamphenicol at 20 μg/ml. To identify clones having lost pCatpUppPthlTakt and possessing an pthl promoter replacement, (clones resistant to 5-FU and sensitive to thiamphenicol) were checked by PCR analysis (with primers takt-0 and takt-5 located outside of the ptal-tkt promoter). Approximately half of the clones had a pthl promoter replacement and half had a wild type ptal-tkt genotype. The C. acetobutylicumΔuppΔcac1502 ΔthlAΔhydA270 ΔpSOL pthl::tal was isolated.

The pNGOP plasmid was constructed to over-express two operons one under the control of the thlA* promoter and containing xfp coding the phosphoketolase and one under the control of the pfk promoter to express the rpiB, rpe and glpX genes coding respectively for a Ribose-5-phosphate isomerase, a Ribulose-5-phosphate-3-epimerase and a Fructose bis phosphate phosphatase The pNGOP vector was constructed in two steps:

1.1 Construction of the Xfp Monocistronic Operon in Vector with an orfH Origin of Replication The xfp gene was PCR amplified with the Phusion DNA polymerase using C. acetobutylicum ATCC824 genomic DNA as template and primers xfp-F and xfp-R. After digestion by BamHI and SfoI, this PCR product was cloned into the pSOS95* plasmid (in this plasmid the −35 region of the thiolase promoter is mutated A→T to decrease the strength of the promoter) previously digested by the same enzymes, giving the pSOS95*::xfp plasmid The orH was PCR amplified with the Phusion DNA polymerase using C. butyricum genomic DNA as template and primers orfh-F and orfh-R. After digestion by ClaI and HindIII, this PCR product was cloned into the pSOS95*::xfp plasmid previously digested by the same enzymes, giving the pORH95*::xfp plasmid

1.2 Construction and Insertion of the NGOP Operon

The pfkA promoter and the glpX (ca_c1088) gene were PCR amplified with the Phusion DNA polymerase using *C. acetobutylicum* ATCC824 genomic DNA as template and respectively primers pfk-F and pfk-R and primers glpx-F and glpx-R on genomic DNA to obtain fragments I and II. These two fragments were fused by PCR using primers pfk-F and glpx-R to yield fragment I/II.

The rpe (ca_c1730) and the rpiB (ca_c2880) genes were PCR amplified with the Phusion DNA polymerase using *C. acetobutylicum* ATCC824 genomic DNA as template and respectively primers rpe-F and rpe-R and primers rpi-F and rpi-R on genomic DNA to obtain fragments III and IV.

The fragments I/II, III and IV were directly cloned into the HindIII linearized pCR4-TOPO by homologous recombination using the GeneArt® Seamless Cloning & Assembly kit to yield the pTOPO-NGOP plasmid. The whole NGOP operon was PCR amplified with the Phusion DNA polymerase using pTOPO-NGOP DNA as template and primers ngop-F and ngop-R as primers. The NGOP operon was directly cloned into the PstI linearized pORH95*::xfp plasmid by homologous recombination using the GeneArt® Seamless Cloning & Assembly kit to yield the pNGOP.

pNGOP.plasmid was used to transform by electroporation the *C. acetobutylicum* ΔuppΔcac1502 ΔthlAΔhydA270 ΔpSOL pthl::tal strain. After selection on Petri plates for clones resistant to erythromycin at 40 µg/ml, *C. acetobutylicum*ΔuppΔcac1502 ΔthlAΔhydA270 ΔpSOL pthl::tal (pISOB) was obtained.

| Name | SEQ ID No | Primer sequence |
|---|---|---|
| Takt-1 | 72 | AAAGGATCCCGTAATGTTGCAGTTACAGAGGGAG |
| Takt-2 | 73 | GGGGGAGGCCTAAAAAGGGGGAAAAAAAGCTTTGTTTTAAATAAGTGTTCTTTATATACTTATTC |
| Takt-3 | 74 | CCCCCTTTTTAGGCCTCCCCCTATAGGAGGCATAAGCAATGAAACTTTTTATAG |
| Takt-4 | 75 | AAAGGATCCCTTGCATATTCCTTGTCCTAAAGGTCC |
| Pthl-1 | 76 | ACAAAGCTTTTTTCCCCCTTTTTAGGTTTTTAACAAAATATATTGATAAAAATAATAATAGTGGG |
| Pthl-2 | 77 | CTTATGCCTCCTATAGGGGAGGTACGGGGTAACAGATAAACCATTTC |
| Takt-0 | 78 | GGATTATATGAACTTACATCAAAGTGCTC |
| Takt-5 | 79 | CATCCACTTTGATAACCTGCCATCCG |
| orfh-F | 80 | AAAAAAAAATCGATAATATGGAACCCGAATTCCGGCATTCAC |
| orfh-R | 81 | AAAAAAAAAGCTTCTTTGGACGTAGTTTGCCCATAGATGAAC |
| xfp-F | 82 | AAAAAAAGGCGCCTTATACATGCCACTGCCAATTAGTTATTTCTGGC |
| xfp-R | 83 | AAAAAAAGGATCCATGAATTCATAATTAATGATTATAAATTTAGGAGGAATATTATGCAAAGTATAATAGGAAAACATAAG |
| pfk-F | 84 | CCCTCACTAAAGGGACTAGTCCTGCAGGTTTAAACGAATTCGCCCTTAGGCCTCTCGAGTTAAAAGTAGGTGTTTTGTACATAATAATATCAGAAGGTAAACACATAATTACTATGG |
| Pfk-R | 85 | CCTTGATTATATTAAACATTTGTTTATAAACACATTGCAACCCCGCGGATGACCGCAGGGACTTAATTTGTCCCAG |
| glpx-F | 86 | CTGGGACAAATTAAGTCCCTGCGGTCATCCGCGGGGTTGCAATGTGTTTATAAACAAATGTTTAATATAATCAAGG |
| glpx-F | 87 | ACTCCTCCCTAACTTTTATTTTTAATTACTCATTGCCGGCTTATTCTACCACTAATTTACTTTTATTCAAGTCATGAATAGC |
| rpe-F | 88 | *ATAAAAGTAAATTAGTGGTAGAATAAGCCGGCATAAATAACGACAAGCACACAGAGGAGGTAGAGATGATAAAATTGGCAGCATCAATTTTATCCGCAGA* |
| rpe-R | 89 | CTCCTATTGATAAGTACGATATAGAAACTAGTCTAAATACTTCCCTTTAATAACTCTATATTTTTTTGATATCGC |
| rpi-F | 90 | GTGCAAATGCATATTATGGTCAAAAAACAAAGTAAACTAGTTTCTATATCGTACTTATCAATAGGAGGTACACTAAATGAAGATAGCAATAGGTAGTGATCATGCAGGATTTTC |
| rpi-R | 91 | TTAGCGGCCGCGAATTCGCCCTTCCCGGGTGCTTCATGAAGCTAATATAATGAAGCAAAGACTATTTTACATTCTTTATTTTGCTAGCTTATTTCATTCCTCCATTGTATTTTTTTCTATTTGTGTAATCTTGTC |
| ngop-F | 92 | GCCGAGAAAACTATTGGTTGGAATGGCGTGTGTGTTAGCCAAAGCTCAGGCCTCTCGAGTTAAAAGTAGGTGTTTTGTACATAATAATATCAG |

| Name | SEQ ID No | Primer sequence |
|---|---|---|
| ngop-R | 93 | ATTATTTTAATCAATATATTTTGTTAAAAAGTACCCGGGTGCTTCATGAAGCT AATATAATGAAGCAAAGACTATTTTACATTCTTTATTTTGCTAGCTTATTTCAT TCCTCCATTGTATTTTTTTCTATTTGTG |

2—Improvement of the Acetate Yield by Inactivation of gapC in C. acetobutylicumΔuppΔcac1502 ΔthlAΔhydA270 ΔpSOL pthl::tal (pNOGP)

Two DNA fragments surrounding the GapC coding sequence (CAC0709) were PCR amplified with the Phusion DNA polymerase with total DNA from C. acetobutylicum as template and two specific couples of olignonucleotides as primers. With the couples of primers gapc-1-gapc-2 and gapc-3-gapc-4, 1008 bp and 1074 bp DNA fragments were respectively obtained. Both primers ldh-1 and gapc-4 introduce a BamHI site while primers gapc-2 and gapc-3 have complementary 5' extended sequences which introduce a StuI site. DNA fragments gapc-1-gapc-2 and gapc-3-gapc-4 were joined in a PCR fusion experiment with primers ldh-1 and ldh-4 and the resulting fragment was cloned in the pCR4-TOPO-Blunt vector to yield pTOPO:gapC. The gapC replacement cassette obtained after BamHI digestion of the resulting plasmid was cloned, at the BamHI, site into pCatUpp to yield the pCatUppΔgapC plasmid.

The pCatUppΔgapC plasmid was used to transform by electroporation C. acetobutylicumΔuppΔcac1502 ΔthlAΔhydA270 ΔpSOL pthl::tal (pNOGP). After selection on Petri plates for clones having inserted the pCatUppΔcgapC plasmid by homologous recombination (resistant to thiamphenicol 20 μg/ml), two colonies were cultured for 24 hours in liquid MS xylose medium and then subcultured in liquid 2YTX medium without antibiotic. Appropriate dilutions were plated on RCA with 5-FU at 400 μM. To select integrants having excised and lost pCatUppΔgapC, 5-FU resistant clones were replica plated on both RCA+5FU and RCA with thiamphenicol at 40 μg/ml. To identify clones having lost pCatUppΔgapC and possessing a markerless gapC deletion, clones resistant to 5-FU and sensitive to thiamphenicol were checked by PCR analysis (with primers gapC-0 and gapC-5 located outside of the gapC replacement cassette and primers gapC-F and gapC-R located inside of gapC). Less than 10% of the clones had a gapC deletion all the other clones having a wild type genotype for gapC. The C. acetobutylicumΔuppΔcac1502 ΔthlAΔhydA270 ΔpSOL pthl::tal ΔgapC (pNOGP) strain was isolated.

The strain was evaluated in MS xylose batch culture as described in example 2. Acetate was the major product with small amount of glycerol.

| Name | SEQ ID NO | Primer sequence |
|---|---|---|
| gapC-1 | 94 | AAAAGGATCCAGGAATGTCAGTTACAAAAGACG |
| gapC-2 | 95 | GGGGGAGGCCTAAAAAGGGGGCATTCTAACTACCTCCAAAAATTTTTTAATATC |
| gapC-3 | 96 | CCCCCTTTTTAGGCCTCCCCCCTAGTTTAAAGCGCTCATTAATTAATTTGAATAG |
| gapC-4 | 97 | AAAAGGATCCGAGTCTTTGGTCCAATATCTAATCCC |
| gapC-0 | 98 | GGACTATATATGTCCAGCGAGGTG |
| gapC-5 | 99 | AGCAGCACTGTCTCCTCCACC |
| gapC-D | 100 | AGAAGGAGCTTTCGTAGTAAACGG |
| gapC-R | 101 | GTGTATCCAAATGATTCATCAGCAGC |

Example 11: Construction of a Clostridium acetobutylicum Strain Unable to Produce Hydrogen and Producing Acetone at High Yield C. acetobutylicumΔuppΔcac1502 ΔthlAΔhydA270 ΔpSOL pthl::tal ΔgapC (pNOGP) produced acetate at high yield. In order to obtain a strain that produces acetone at high yield, the ptb and buk genes encoding the last two enzymatic steps of the butyrate pathway were first deleted. Then to allow acetone production the synthetic atoB gene coding for the thiolase of Escherichia coli was introduced at the ΔthlA locus. Finally the synthetic acetone pathway was expressed from plasmid pCLF95 (Dusseaux et al 2013).

1. Deletion of the Ptb and Buk Genes Encoding the Last Two Steps of the Butyrate Pathway in Clostridium acetobutylicumΔuppΔcac1502 ΔthlAΔhydA270 ΔpSOL pthl::tal ΔgapC (pNOGP)

The pCatUppΔptbbuk plasmid was used to transform by electroporation C. acetobutylicumΔuppΔcac1502 ΔthlAΔhydA270 ΔpSOL pthl::tal ΔgapC (pNOGP). After selection on Petri plates for clones having inserted the pCatUppΔptbbuk plasmid by homologous recombination (resistant to thiamphenicol 20 μg/ml), two colonies were cultured for 24 hours in liquid MS xylose medium and then subcultured in liquid 2YTX medium without antibiotic. Appropriate dilutions were plated on RCA with 5-FU at 400 μM. To select integrants having excised and lost pCatUppΔptbbuk, 5-FU resistant clones were replica plated on both RCA+5FU and RCA with thiamphenicol at 40 μg/ml. To identify clones having lost pCatUppΔptbbuk and possessing a markerless ptb-buk deletion, clones resistant to 5-FU and sensitive to thiamphenicol were checked by PCR analysis (with primers ptuk-0 and ptuk-5 located outside of the ptb-buk replacement cassette and primers ptuk-F and ptuk-R located inside of ptb). Approximately half of the clones had a ptb-buk deletion and half had a wild type genotype for ptb-buk. C. acetobutylicumΔuppΔcac1502 ΔthlAΔhydA270 ΔpSOL pthl::tal ΔgapC Δptb-buk (pNOGP) was isolated.

2. Insertion of a Synthetic atoB Gene at the ΔthlA Locus of C. acetobutylicumΔuppΔcac1502 ΔthlAΔhydA270 ΔpSOL pthl::tal ΔgapC Δptb-buk (pNOGP)

The pEryUppAtoB plasmid of example was digested by BamHI and the atoB expression-insertion cassette was cloned at the BamHI site of the pCatUpp plasmid to yield pCatUppAtoB. pCatUppAtoB was used to transform by electroporation C. acetobutylicumΔuppΔcac1502 ΔthlAΔhydA270 ΔpSOL pthl::tal ΔgapC Δptb-buk (pNOGP). After selection on Petri plates for clones having inserted the pCatUppAtoB plasmid by homologous recombination (resistant to thiamphenicol 20 μg/ml), two colonies were cultured for 24 hours in liquid MS Xylose medium and then subcultured in liquid 2YTX medium without antibiotic. Appropriate dilutions were plated on RCA with 5-FU at 400 μM. To select integrants having excised and lost pCatpUppAtoB, 5-FU resistant clones were replica plated on both RCA+5FU and RCA with thiamphenicol at 40 μg/ml. To identify clones having lost pcatUppAtoB and possessing an atoB insertion, (clones resistant to 5-FU and sensitive to thiamphenicol) were checked by PCR analysis (with primers thla-0 and thla-5 located outside of the ΔthlA locus and primers atoB-F and atoB-R located inside of atoB). Less than 10% of the clones had an atoB insertion all the other clones having a ΔthlA genotype. The C. acetobutylicumΔuppΔcac1502 ΔthlAΔhydA270 ΔpSOL pthl::tal ΔgapC Δptb-buk ΔthlA::atoB (pNOGP) was isolated. 3. Construction of C. acetobutylicumΔuppΔcac1502 ΔthlAΔhydA270 ΔpSOL pthl::tal ΔgapC Δptb-buk ΔthlA::atoB (pNOGP, pCLF95) Strain In the pSOS95 plasmid pCLF95 (Dusseaux et al 2013), the ctfA-B (CAP163-164), and adc (CAP165) genes are expressed from the thlA promoter. The pCLF95 plasmid was constructed by inserting the SalI fragment containing the acetone operon at the SalI site of the pCLF1 plasmid (Dusseaux et al 2013).

The pCLF95 plasmid was used to transform by electroporation the C. acetobutylicumΔuppΔcac1502 ΔthlAΔhydA270 ΔpSOL pthl::tal ΔgapC Δptb-buk ΔthlA::atoB (pNOGP) strain. After selection on Petri plates for clones having containing the two replicative plasmids (resistant to erythromycin at 40 μg/ml and thiamphenicol at 40 μg/ml), 10 colonies were cultured for 24 hours in liquid 2YTX medium and then subcultured in liquid MS Xylose medium. The clone having the fastest growth in MS xylose medium was designated C. acetobutylicumΔuppΔcac1502 ΔthlAΔhydA270 ΔpSOL pthl::tal ΔgapC Δptb-buk ΔthlA::atoB (pNOGP, pCLF95)

The strain was evaluated in MS xylose batch culture as described in example 2. Acetone was the major product with small amount of acetate and glycerol.

Example 12: Construction of a Clostridium acetobutylicum Strain Unable to Produce Hydrogen and Producing Isopropanol at High Yield C. acetobutylicumΔuppΔcac1502 ΔthlAΔhydA270 ΔpSOL pthl::tal ΔgapC Δptb-buk ΔthlA::atoB (pNOGP, pCLF95) produced acetone at high yield. In order to obtain a strain that produces isopropanol at high yield, the pCLF952 plasmid (Dusseaux et al 2013) in which ctfA-B (CAP163-164), sadh (from C. beijerinckii), adc (CAP165) are expressed from the thlA promoter, was used to transform by electroporation the C. acetobutylicumΔuppΔcac1502 ΔthlAΔhydA270 ΔpSOL pthl::tal ΔgapC Δptb-buk ΔthlA::atoB (pNOGP) strain. After selection on Petri plates for clones containing the two replicative plasmids (resistant to erythromycin at 40 μg/ml and thiamphenicol at 40 μg/ml), 10 colonies were cultured for 24 hours in liquid 2YTX medium and then subcultured in liquid MS xylose medium. The clone having the fastest growth in MS xylose medium was designated C. acetobutylicumΔuppΔcac1502 ΔthlAΔhydA270 ΔpSOL pthl::tal ΔgapC Δptb-buk ΔthlA::atoB (pNOGP pCLF952) The strain was evaluated in MS xylose batch culture as described in example 2. Isopropanol was the major product with small amount of acetate and glycerol.

Example 13: Construction of a Clostridium acetobutylicum Strain Unable to Produce Hydrogen and Producing 1, 3 Butanediol at High Yield The C. acetobutylicumΔuppΔcac1502 ΔthlA::atoBΔhydA270 ΔldhA Δptb-buk strain produced n-butanol at high yield. In order to obtain a strain that produces 1,3 butanediol, i) the adhE2 gene was replaced by an evolved adhE2 gene (adhE2*) to get an AdhE2 enzyme that can convert S-3-hydroxybutyryl-CoA to 1, 3 butanediol, ii) an "homologous non oxidative glycolytic pathway" was expressed from a plasmid the expressing the xfp (CAC1343), glpX (CAC1088), rpiB (CAC2880) and rpe (CAC1341) genes and from the chromosome by introducing a synthetic promoter in front of the tal-tkt (CAC1347-1348) operon, iii) by inactivating the crt gene encoding the crotonase and deleting the "sol operon" on the pSOL1 plasmid.

1—Evolution of AdhE2 and Construction of the C. acetobutylicumΔuppΔcac1502 ΔthlA::atoBΔhydA270 ΔldhA Δptb-buk (pTLSadhE2*) Strain.

The pE5α plasmid was introduced in E. coli MG1655 and the recombinant strain was subject to UV and EMS mutagenesis before plating the cells on M9 with S-1, 3 butanediol as a carbon source. 10 individual colonies were evaluated for growth in M9 medium with S-1, 3 butanediol as the carbon source. From the clones giving the highest growth, the pE5α* plasmid was extracted and the mutated adhE2 gene sequenced and named adhE2*. The pTLSadhE2* plasmid was constructed by inserting the SalI fragment of pE5α* containing the adhE2*operon at the SalI site of the pTLS1 plasmid (Harris et al 2000).

The pTLSadhE2* plasmid was used to transform by electroporation the C. acetobutylicumΔuppΔcac1502 ΔthlA::atoBΔhydA270 ΔldhA Δptb-buk strain. After selection on Petri plates for clones resistant to tetracycline at 10 μg/ml, C. acetobutylicumΔuppΔcac1502 ΔthlA::atoBΔhydA270 ΔldhA Δptb-buk (pTLSadhE2*) strain was obtained 2—Construction of C. acetobutylicumΔuppΔcac1502 ΔthlA::atoBΔhydA270 ΔldhAΔptb-buk pthl::tal (pNOGP, pTLSadhE2*)

The pNGOP plasmid was used to transform by electroporation the C. acetobutylicumΔuppΔcac1502 ΔthlA::atoBΔhydA270 ΔldhA Δptb-buk (pTLSadhE2*) strain. After selection on Petri plates for clones resistant to erythromycin at 40 μg/ml and tetracycline at 10 μg/ml, C. acetobutylicumΔuppΔcac1502 ΔthlA::atoBΔhydA270 ΔldhA Δptb-buk (pNOGP, pTLSadhE2*) strain was obtained 3—Construction of C. acetobutylicumΔuppΔcac1502 ΔthlA::atoBΔhydA270 ΔldhAΔptb-buk Δcrt pthl::tal (pNOGP, pTLSadhE2*)

Two DNA fragments surrounding the crotonase coding sequence (CAC2712) were PCR amplified with the Phusion DNA polymerase with total DNA from C. acetobutylicum as template and two specific couples of olignonucleotides as primers. With the couples of primers crt-1-crt-2 and crt-3-crt-4, 1023 bp and 1015 bp DNA fragments were respectively obtained. Both primers crt-1 and crt-4 introduce a BamHI site while primers crt-2 and crt-3 have complementary 5' extended sequences which introduce a StuI site. DNA fragments crt-1-crt-2 and crt-3-crt-4 were joined in a PCR fusion experiment with primers crt-1 and crt-4 and the resulting fragment was cloned in the pCR4-TOPO-Blunt vector to yield pTOPO:crt. The crt replacement cassette obtained after BamHI digestion of the resulting plasmid was cloned, at the BamHI, site into pCatUpp to yield the pCatUppΔcrt plasmid.

The pCatUppΔcrt plasmid was used to transform by electroporation C. acetobutylicumΔuppΔcac1502 ΔthlA::atoBΔhydA270 ΔldhAΔptb-buk pthl::tal (pNOGP, pTLSadhE2*). After selection on Petri plates for clones having inserted the pCatUppΔcrt plasmid by homologous recombination (resistant to thiamphenicol 20 µg/ml, erythromycin 40 µg/ml and tetracycline at 10 µg/ml), two colonies were cultured for 24 hours in liquid MS Glucose medium and then subcultured in liquid 2YTG medium with erythromycin 40 µg/ml and tetracycline at 10 µg/ml. Appropriate dilutions were plated on RCA with 5-FU at 400 µM and erythromycin 40 µg/ml and tetracycline at 10 µg/ml. To select integrants having excised and lost pCatUppΔcrt, 5-FU resistant clones were replica plated on both RCA+5FU and RCA with thiamphenicol at 40 µg/ml. To identify clones having lost pCatUppΔcrt and possessing a markerless crt deletion, clones resistant to 5-FU and erythromycin and sensitive to thiamphenicol were checked by PCR analysis (with primers crt-0 and crt-5 located outside of the crt replacement cassette and primers crt-F and crt-R located inside of crt). Less than 5% of the clones had a crt deletion all the other clones having a wild type genotype for crt. The C. acetobutylicumΔuppΔcac1502 ΔthlA::atoBΔhydA270 ΔldhAΔptb-bukΔcrt pthl::tal (pNOGP, pTLSadhE2*) was isolated.

4—Construction of C. acetobutylicum ΔuppΔcac1502 ΔthlA::atoBΔhydA270 ΔldhAΔptb-buk Δcrt ΔpSOL pthl::tal (pNOGP, pTLSadhE2*)

In order to obtain a strain that produce 1, 3 butanediol at high yield, the pSOL1 megaplasmid was cured from the C. acetobutylicumΔuppΔcac1502 ΔthlA::atoBΔhydA270 ΔldhAΔptb-bukΔcrt pthl::tal (pNOGP, pTLSadhE2*) strain by serial subcultures (20) in MS glucose medium. Cells having lost the pSOL1 megaplasmid were identified on RCA agar plates containing starch (2%) and glucose (0.2%) and after iodine staining as they do not produce halo of starch hydrolysis (Sabathe et al, 2002). Approximately 1 colony out of 1000 has lost the pSOL1 megaplasmid after 20 subcultures. The C. acetobutylicumΔuppΔcac1502 ΔthlA::atagΔhydA270 ΔldhAΔptb-buk Δcrt ΔpSOL pthl::tal (pNOGP, pTLSadhE2*) strain was obtained. The strain was evaluated in MS glucose batch culture as described in example 2. 1, 3 butanediol was the major product with small amount of ethanol and acetate.

REFERENCES

Cooksley C. M., Zhang Y, Wang H, Redl S, Winzer K, Minton N. P. (2012) Targeted mutagenesis of the Clostridium acetobutylicum acetone-butanol-ethanol fermentation pathway. Met. Eng. 14:630-41.

Dusséaux 51, Croux C, Soucaille P, Meynial-Salles I. (2013) Metabolic engineering of Clostridium acetobutylicum ATCC 824 for the high-yield production of a biofuel composed of an isopropanol/butanol/ethanol mixture. Met. Eng. 18:1-8.

Harris L M, Welker N E, Papoutsakis E T (2002), Northern, morphological and fermentation analysis of spo0A inavtivation and overexpression in C. acetobutylicum ATCC824. J Bacteriol., 184:3586-97.

Heap, J T, Kuehne, S A, Ehsaan, M, Cartman, S T, Cooksley, C M, Scott, J C, and N. P. Minton. 2010. The ClosTron: Mutagenesis in refined and streamlined. J Microbiol Methods, 80(1):49-55.

B. H. Kim, P. Bellows, R. Datta and J. G. Zeikus (1984) Control of Carbon and Electron Flow in Clostridium acetobutylicum Fermentations: Utilization of Carbon Monoxide to Inhibit Hydrogen Production and to Enhance Butanol Yields. Appl. Env. Microbiol. 48: 764-770.

| Name | SEQ ID NO | Primer sequence |
|---|---|---|
| crt-1 | 102 | AAAAGGATCCGTAAAAAGGATAGTGTAATTGAATAATAATGTGG |
| crt-2 | 103 | GGGGGAGGCCTAAAAAGGGGGCATGACTAATCCTCCTAAAATATTTTTTATTG |
| crt-3 | 104 | CCCCCTTTTTAGGCCTCCCCCTAGGAGGTAAGTTTATATGGATTTTAATTTAACAAGAG |
| crt-4 | 105 | AAAAGGATCCGCATGAAGCTTAGCTCTTGCAGC |
| crt-0 | 106 | GTAGCTTTTGCCTATATTTTTGCAGC |
| Crt-5 | 107 | CAACTATATTCATCCTCTTAACCTCC |
| crt-F | 108 | CACTAAAAGAAATGGATTATGTTATAGGTG |
| crt-R | 109 | GCTAAAGCAGTATCAATATCACACTGC |

Nakhamanovich, B. M., and N. A. Sticheblykina. 1959. Fermentation of pentoses of corn cob hydrolyzates by *Clostridium acetobutylicum*. Mikrobiologiya 28:91-96

Nolling J., Breton, G., Omelchenko M. V., Makarova K. S., Zeng Q., Gibson R., Lee H. M., Dubois J., Qui D., Hitti J., GTC Sequencing, Center Production, Finishing, and Bioinformatics Teams, Wolf Y. I., Tatusov R. L., Sabathe F., Doucette-Stamm L., Soucaille P., Daly M. J., Bennett G. N., Koonin E. V. and D. R. Smith. 2001. Genome sequence and comparative analysis of the solvent producing bacterium *Clostridium acetobutylicum*. J. Bacteriol. 183:4823-4838.

Raynaud C., Sarcabal P., Meynial-Salles I., Croux C. and Soucaille P. (2003). Molecular characterization of the 1,3-propanediol operon of *Clostridium butyricum* encoding a novel coenzyme B12-independent glycerol dehydratase and a 1,3-propanediol dehydrogenase. Proc. Natl. Acad. Sci. 100, 5010-5015.

Sonderegger M. and Sauer U., 2003. Evolutionary Engineering of *Saccharomyces cerevisiae* for Anaerobic Growth on Xylose. Appl. Env. Microbiol. 69: 1990-1998.

Soni et al, 1987, *Appl. Microbiol. Biotechnol.* 27:1-5.

Soucaille, P., Figge, R. and C. Croux. 2006. Process for chromosomal integration and DNA sequence replacement in clostridia. PCT/EP2006/066997.

Tamaru, Y., S. Karita, A. Ibrahim, Compere, A. L., and W. L. Griffith. 1979. Evaluation of substrates for butanol production. Dev. Ind. Microbiol. 20:509-517.

Weber, C., Farwick, A., Benisch, F., Brat, D., Dietz, H., Subtil, T. and E. Boles. 2010. Trends and challenges in the microbial production of lignocellulosic bioalcohol fuels. Appl. Microbiol. Biotechnol. 87: 1303-1315.

The invention claimed is:

1. A genetically modified *Clostridium acetobutylicum* unable to produce hydrogen, wherein the main [Fe—Fe]-hydrogenase encoding gene (hydA) and the main thiolase encoding gene (thlA) are attenuated to such an extent that the genetically modified *Clostridium acetobutylicum* is unable to produce hydrogen.

2. The genetically modified *Clostridium acetobutylicum* according to claim 1, wherein the main [Fe—Fe]-hydrogenase encoding gene (hydA) and the main thiolase encoding gene (thlA) are inactivated.

3. The genetically modified *Clostridium acetobutylicum* according to claim 1, wherein it comprises at least one additional modification to produce lactate as the main product.

4. The genetically modified *Clostridium acetobutylicum* according to claim 3, wherein the at least one additional modification comprises attenuation of at least one gene involved in the ethanol formation pathways selected in the group comprising adhE1 and adhE2.

5. The genetically modified *Clostridium acetobutylicum* according to claim 3, wherein it comprises at least one additional modification to produce isobutanol as the main product.

6. The genetically modified *Clostridium acetobutylicum* according to claim 5, wherein the at least one additional modification to produce isobutanol as the main product comprises the overexpression of at least one gene comprised in the group consisting of homologous acetolactate synthase encoding gene, homologous ketoacid reducto-isomerase encoding gene, homologous dihydroxy acid dehydratase encoding gene, homologous ketoacid decarboxylase encoding gene and homologous alcohol dehydrogenase encoding gene.

7. The genetically modified *Clostridium acetobutylicum* according to claim 5, wherein the at least one additional modification comprises attenuation of at least one gene involved in the lactate formation pathways which is selected in the group comprising IdhA, IdhB, IdhC and IdhD.

8. The genetically modified *Clostridium acetobutylicum* according to claim 3, wherein it comprises at least one additional modification to convert glycerol to 1, 3 propanediol as the main product.

9. The genetically modified *Clostridium acetobutylicum* according to claim 8, wherein the at least one additional modification comprises the expression of heterologous genes coding for a B12-independent diol-dehydratase and a 1,3 propanediol dehydrogenase.

10. The genetically modified *Clostridium acetobutylicum* according to claim 3, wherein it comprises at least one additional modification for the production of acetate as the main product.

11. The genetically modified *Clostridium acetobutylicum* according to claim 10, wherein the at least one additional modification to produce acetate as the main product comprises the overexpression of at least one gene comprised in the group consisting of homologous Fructose bis phosphate phosphatase encoding gene, homologous Ribose-5-phosphate isomerase encoding genes, homologous Ribulose-5-phosphate 3-epimerase encoding gene, homologous Transketolase encoding genes, homologous Transaldolase encoding gene and homologous Phosphoketolase encoding gene.

12. The genetically modified *Clostridium acetobutylicum* according to claim 10, wherein the at least one additional modification to produce acetate as the main product comprises the attenuation of at least one gene comprised in the group consisting of PhosphoFructokinase encoding genes, Glucose PTS encoding gene and NAD+ dependent Glyceraldehyde-3-Phosphate dehydrogenase encodinggene.

13. The genetically modified *Clostridium acetobutylicum* according to claim 12, wherein it comprises at least one further additional modification for the production of acetone as the main product.

14. The genetically modified *Clostridium acetobutylicum* according to claim 13, wherein it comprises at least one further additional modification for the production of isopropanol as the main product.

15. The genetically modified *Clostridium acetobutylicum* according to claim 13, wherein it comprises at least one further additional modification for the production of 3-hydro-3-methylbutyrate as the main product.

16. The genetically modified *Clostridium acetobutylicum* according to claim 15, wherein it comprises at least one additional modification for the production of isobutene as the main product.

17. The genetically modified *Clostridium acetobutylicum* according to claim 1, wherein it comprises at least one additional modification to produce ethanol as the main product.

18. The genetically modified *Clostridium acetobutylicum* according to claim 17, wherein the at least one additional modification to produce ethanol as the main product comprises attenuation of at least one gene involved in the lactate formation pathways selected in the group comprising IdhA, IdhB, IdhC and IdhD.

19. The genetically modified *Clostridium acetobutylicum* according to claim 17, wherein it comprises at least one additional modification to produce n-butanol as the main product.

20. The genetically modified *Clostridium acetobutylicum* according claim 19, wherein the at least one additional modification comprises expressing a gene encoding a heterologous thiolase less inhibited by CoASH than ThlA.

21. The genetically modified *Clostridium acetobutylicum* according to claim 20, wherein the gene encoding a heterologous thiolase comprises an optimized synthetic gene encoding the AtoB thiolase from *Escherichia coli*.

22. The genetically modified *Clostridium acetobutylicum* according to claim 19, wherein at least one of the genes ptb and buk encoding for the final two steps of butyrate formation is attenuated.

23. The genetically modified *Clostridium acetobutylicum* according to claim 19, wherein it comprises at least one additional modification for the production of 1, 3 butanediol as the main product.

* * * * *